United States Patent
Hou et al.

(10) Patent No.: US 8,293,773 B2
(45) Date of Patent: Oct. 23, 2012

(54) 1, 2, 3-TRIAZOLE DERIVATIVES AS NEW CANNABINOID-1 RECEPTOR ANTAGONISTS

(75) Inventors: Duen-Ren Hou, Taipei (TW); Ming-Shiu Hung, Luzhu Township, Taoyuan County (TW); Chun-Chen Liao, Baoshan Township, Hsinchu County (TW); Chun-Cheng Lin, Fengyuan (TW)

(73) Assignee: National Tsing Hua University, Hsinchu (TW)

( * ) Notice: Subject to any disclaimer, the term of this patent is extended or adjusted under 35 U.S.C. 154(b) by 98 days.

(21) Appl. No.: 12/591,235

(22) Filed: Nov. 13, 2009

(65) Prior Publication Data
US 2010/0144734 A1     Jun. 10, 2010

Related U.S. Application Data

(60) Provisional application No. 61/193,498, filed on Dec. 4, 2008.

(51) Int. Cl.
*A61K 31/4192* (2006.01)
*C07D 249/06* (2006.01)

(52) U.S. Cl. .................................... 514/359; 548/255

(58) Field of Classification Search .................. 514/359; 548/255
See application file for complete search history.

(56) References Cited

FOREIGN PATENT DOCUMENTS

| | | |
|---|---|---|
| EP | 1921072 A1 * | 5/2008 |
| EP | 1921072 A1 * | 5/2008 |
| EP | 1921072 (A1) | 5/2008 |
| TW | 285197 (B) | 8/2007 |
| UA | 80298 (C2) | 9/2007 |
| WO | WO03082833 (A1) | 10/2003 |
| WO | WO2006030285 (A1) | 3/2006 |

OTHER PUBLICATIONS

Hou, et al., Bio. & Med. Chem. Lett., 19, 2009, pp. 1022-1025.*
Duen-Ren Hou, Safiul Alam, Ting-Chun Kuan, Mani Ramanathan, Tsung-Pang Lin and Ming-Shiu Hung; 1,2,3-Triazole derivatives as new cannabinoid CB1 receptor antagonists; Bioorganic & Medicinal Chemistry Letters; Feb. 1, 2009; pp. 1022-1025; vol. 19, Issue 3.

* cited by examiner

*Primary Examiner* — Susannah Chung
(74) *Attorney, Agent, or Firm* — Bacon & Thomas, PLLC

(57) ABSTRACT

The present invention relates to 1,2,3-triazole derivatives which can be used as cannabinoid CB1 receptor antagonists. In addition, the compound of the 1,2,3-triazole derivatives in the present invention can be formulated into a pharmaceutical composition for treating indications relative to signal transduction of CB1 receptors.

5 Claims, No Drawings

1,2,3-TRIAZOLE DERIVATIVES AS NEW CANNABINOID-1 RECEPTOR ANTAGONISTS

BACKGROUND OF THE INVENTION

1. Field of the Invention

The present invention relates to 1,2,3-triazole derivatives and, more particularly, to those capable of being used as cannabinoid CB1 receptor antagonists.

2. Description of Related Art

Obesity caused by an imbalance between food intake and energy expenditure, is a significant risk factor for cardiovascular disease and diabetes, and associated with significantly reduced life longevity. The World Health Organization (WHO) declared that obesity has become a global epidemic posing a serious threat to public health. The short-term diet or exercise is not effective as most obese patients readily regain their lost weight thereafter. Therefore, the medical treatment of obesity is an attractive approach.

In this respect, cannabinoid-1 receptor (CB1R) and its endogenous ligands (agonists), the endocannabinoids, have been found to be involved in the control of weight via a dual mechanism of food intake modification and the regulation of energy homeostasis. Indeed, the biological effects of the CB1 receptors, which are mainly located within the central nervous system, can be mediated through exposure to agonists or antagonists (inverse agonists). Blocking the effects of the endogenous cannabinoids has become a therapeutic avenue to treat obesity.

The other known cannabinoid receptor (CB2R), is predominantly found in the immune system and related to immune regulation. Therefore, good CB1/CB2 selectivity is a desired feature for the development of new anti-obesity drug. The most clinically advanced CB1 receptor antagonist, Rimonabant (SR141716A) launched by Sanofi-Aventis, binds to the human CB1 receptor with $5.6\pm0.5$ nM ($K_i$) affinity (formula A). Since that development, many small molecule CB1 antagonists with diverse chemical structures have been prepared and reviewed. For example, Ibipinabant (SLV319), Otenabant (CP-945,598) and Taranabant (MK-0364) have been reported to be in various phases of clinical trials.

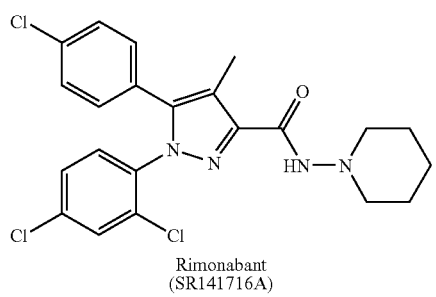

Formula A

Rimonabant
(SR141716A)

In addition to the pyrazole core of SR141716A, derivatives of other five-membered heterocycles, such as pyrrole, thiophene, thiazole, imidazole, oxazole, and 1,2,4-triazole are also known as the CB1 receptor antagonists. However, whether the derivatives of 1,2,3-triazole serve as CB1 receptor antagonists has not been explored yet.

SUMMARY OF THE INVENTION

The object of the present invention is to provide the derivatives of 1,2,3-triazole which can function as cannabinoid-1 (CB1) receptor antagonists.

To achieve the object, the present invention provides a compound of formula I and pharmaceutically acceptable salts, prodrugs and solvates thereof,

wherein Ar is

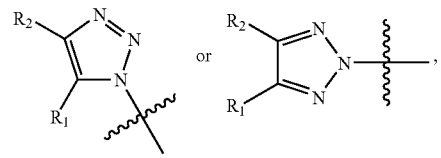

in which $R_1$ and $R_2$ each independently represent H, phenyl, thienyl or pyridyl, unsubstituted or substituted by halo, hydroxy, cyano, nitro, thiohydroxy, amino, carbonyl, carbamoyl, sulfamoyl, $C_{1-4}$ alkyl, $C_{2-4}$ alkenyl, $C_{2-4}$ alkynyl, $C_{1-4}$ alkoxy, $C_{1-4}$ alkyl alcohol, $C_{1-4}$ haloalkyl, $C_{1-4}$ haloalkylthio, $C_{1-4}$ alkylamino, $C_{1-4}$ alkylamido, $C_{1-4}$ alkylsulfonyl, $C_{1-4}$ haloalkylsulfonyl, $C_{1-4}$ alkoxycarbonyl or $C_{1-4}$ alkylcarbamoyl, with a proviso that one of $R_1$ and $R_2$ is not H;

X is —$(CH_2)_b$— in which b is 0, 1, 2, 3 or 4;

Y is —C(O)— or —S($O_2$)—; and

Z is —$(CH_2)_r(Ph)_s$ in which s is 1 or 2 and r is 0, 1, 2, 3 or 4, $C_{1-10}$ alkyl, $C_{2-10}$ alkenyl, $C_{2-10}$ alkynyl, $C_{5-9}$ aryl, $C_{4-9}$ cycloalkyl, naphthyl, anthracenyl, $OR_3$, $NR_4R_5$, or $C_{4-9}$ heteroaryl or $C_{3-10}$ heterocycloalkyl comprising one to three heteroatoms which each independently are N, O or S;

$R_3$ is $C_{1-10}$ alkyl, $C_{2-10}$ alkenyl, $C_{2-10}$ alkynyl, —$(CH_2)_r(Ph)_s$, $C_{5-9}$ aryl, $C_{4-9}$ cycloalkyl, naphthyl, anthracenyl, or $C_{4-9}$ heteroaryl or $C_{3-10}$ heterocycloalkyl comprising one to three heteroatoms which each independently are N, O, or S;

$R_4$ and $R_5$ each independently are H,

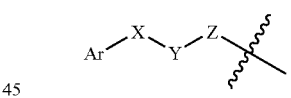

—$(CH_2)_r(Ph)_s$, $C_{1-10}$ alkyl, $C_{2-10}$ alkenyl, $C_{2-10}$ alkynyl, $C_{5-9}$ aryl, $C_{4-9}$ cycloalkyl, carbamoyl, ureido, adamantyl, —$CHR_6R_7$, or $C_{4-9}$ heteroaryl or $C_{3-10}$ heterocycloalkyl comprising one to three heteroatoms which each independently are N, O, or S, in which $R_6$ and $R_7$ each independently are $C_{1-4}$ alkyl alcohol, $C_{1-4}$ alkyl or benzyl, with a proviso that one of $R_4$ and $R_5$ is not H and one of $R_6$ and $R_7$ is not H, wherein $R_6$ and $R_7$ are unsubstituted or optionally substituted by thiohydroxy, hydroxy, phenyl, nitro, or $C_{1-4}$ alkoxy; and $R_3$, $R_4$, $R_5$, ph, $C_{1-10}$ alkyl, $C_{2-10}$ alkenyl, $C_{2-10}$ alkynyl, $C_{5-9}$ aryl, $C_{4-9}$ cycloalkyl, $C_{4-9}$ heteroaryl, $C_{3-10}$ heterocycloalkyl, naphthyl, anthracenyl are unsubstituted or optionally substituted by halo, hydroxy, cyano, nitro, thiohydroxy, amino, carbonyl, carbamoyl, sulfamoyl, $C_{1-4}$ alkyl, $C_{2-4}$ alkenyl, $C_{2-4}$ alkynyl, $C_{1-4}$ alkoxy, $C_{1-4}$ alkyl alcohol, $C_{1-4}$ haloalkyl, $C_{1-4}$ haloalkylthio, $C_{1-4}$ alkylamino, $C_{1-4}$ alkylamido, $C_{1-4}$ alkylsulfonyl, $C_{1-4}$ haloalkylsulfonyl, $C_{1-4}$ alkoxycarbonyl, $C_{1-4}$ alkylcarbamoyl, phenyl or benzyl.

In one aspect of the present invention, Ar is

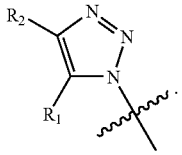

Meanwhile, $R_1$ and $R_2$ each independently are H, phenyl or thienyl, and Y is —C(O)—. Z is —(CH$_2$)$_r$(Ph)$_s$ in which s is 1 or 2 and r is 0, 1, 2, 3 or 4, $C_{1-10}$ alkyl, $C_{2-10}$ alkenyl, $C_{2-10}$ alkynyl, $C_{5-9}$ aryl, $C_{4-9}$ cycloalkyl, naphthyl, anthracenyl, $OR_3$, $NR_4R_5$, or $C_{4-9}$ heteroaryl or $C_{3-10}$ heterocycloalkyl comprising one to three heteroatoms which each independently are N, O or S. Particularly, $R_1$ and $R_2$ are phenyl; $R_3$ is $C_{4-8}$ alkyl or benzyl; and $R_4$ and $R_5$ each independently are H, $C_{1-8}$ alkyl, $C_{2-8}$ alkenyl, six-membered heterocycloalkyl comprising a heteroatom of N, $C_{4-8}$ alkylcarbamoyl or $C_{4-8}$ alkylureido. Besides, $R_1$ and $R_2$ can be optionally substituted by halo, methoxy, methyl, halomethyl, methoxycarbonyl, nitro, or cyano, wherein halo can be F, Cl, or Br.

In another aspect of the present invention, Ar is

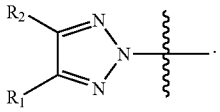

In addition, $R_1$ and $R_2$ are phenyl. Y is —C(O)— and Z is phenyl, halophenyl, $C_{4-8}$ alkyl, $OR_3$, $NR_4R_5$, or $C_{4-5}$ heterocycloalkyl comprising one to two heteroatoms selected from N and O. Particularly, $R_3$ is $C_{2-8}$ alkyl, or phenyl, and $R_4$ and $R_5$ each independently are H, $C_{4-8}$ alkyl, phenyl, benzyl, phenylethyl, phenylpropyl, cyclohexyl, propinylcyclohexyl, $C_{2-4}$ alkoxycarbonylmethyl, adamantyl, six-membered heterocycloalkyl comprising one to two heteroatoms which each independently are N or O. Alternatively, $R_4$ and $R_5$ each independently are

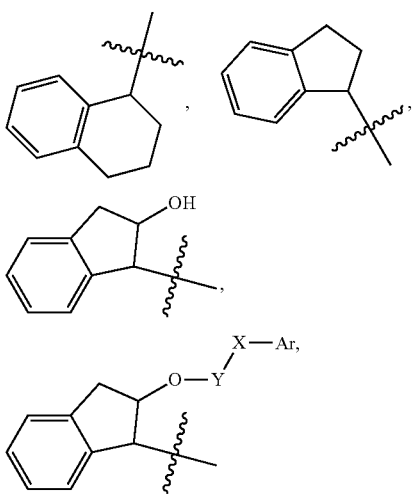

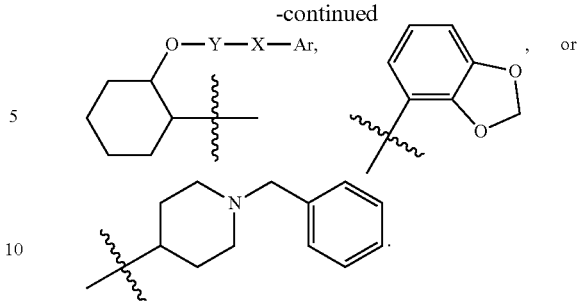

$R_1$ and $R_2$ can be optionally substituted by halo, and halo can be Cl, and $C_{4-8}$ alkyl, phenyl, benzyl, phenylethyl, phenylpropyl, cyclohexyl, propinylcyclohexyl, $C_{2-4}$ alkoxycarbonylmethyl, adamantyl, and six-membered heterocycloalkyl can be substituted by methoxy, methyl, halomethyl or halo.

Pharmaceutically acceptable salts and prodrugs of compounds disclosed herein are within the scope of this disclosure. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxy-substituted alkylamines such as diethanolamine, triethanolamine or tris(hydroxymethyl)-aminomethane), or with bases such as piperidine or morpholine.

Another object of the present invention is to provide a pharmaceutical composition comprising an effective amount of any one compound of the present invention and a pharmaceutical acceptable carrier or diluent. Such a pharmaceutical composition can be used to treat obesity, psychiatric disorders, psychotic disorders, schizophrenia, bipolar disorders, anxiety, anxio-depressive disorders, depression, cognitive disorders, memory disorders, obsessive-compulsive disorders, anorexia, bulimia, attention disorders, epilepsy, neurological disorders, dementia, Parkinson's Disease, Huntington's Chorea, Alzheimer's Disease, immune disorders, cardiovascular disorders, reproductive disorders, endocrine disorders, septic shock, diseases related to the respiratory and gastrointestinal systems, and extended abuse, addiction and/or relapse indications.

Also within the scope of this invention is a method for treating the foregoing indications by administering an effective amount of the abovementioned pharmaceutical composition to a subject in need.

The following definitions apply to the terms as used throughout this specification, unless otherwise limited in specific instances.

The term "$C_{1-10}$ alkyl" as used herein and in the claims (unless specified otherwise) means a saturated aliphatic hydrocarbon including straight chain and branched chain groups, and such a hydrocarbon with 1 to 10 carbon atoms (whenever a numerical range; e.g., "1-10", is stated herein, it means that the group, in this case the alkyl group may contain 1 carbon atom, 2 carbon atoms, 3 carbon atoms, etc. up to and including 10 carbon atoms). More preferably, it is a lower alkyl having 1 to 4 carbon atoms. For example, $C_{1-4}$ alkyl represents methyl, ethyl, propyl, isopropyl, butyl, isobutyl, t-butyl and the like The term "$C_{2-10}$ alkenyl" as used herein and in the claims (unless specified otherwise) means an alkyl group, as defined herein, having at least one carbon-carbon double bond, for example ethenyl, propenyl, isopropenyl, butenyl, isobutenyl, t-butenyl and the like.

The term "$C_{2-10}$ alkynyl" as used herein and in the claims (unless specified otherwise) means an alkyl group, as defined herein, having at least one carbon-carbon triple bond, for example ethynyl, propynyl, isopropynyl, butynyl, isobutynyl, t-butynyl and the like.

The term "$C_{5-9}$ aryl" as used herein and in the claims (unless specified otherwise) means an all-carbon monocyclic or fused-ring polycyclic (i.e., rings which share adjacent pairs of carbon atoms) groups having 5 to 9 carbon atoms and a completely conjugated pi-electron system.

The term "$C_{4-9}$ cycloalkyl" as used herein and in the claims (unless specified otherwise) means an all-carbon monocyclic or fused ring (i.e., rings which share and adjacent pair of carbon atoms) group with 4 to 9 carbon atoms, wherein one or more rings do not have a completely conjugated pi-electron system. Examples, without limitation, of cycloalkyl groups are cyclopropane, cyclobutane, cyclopentane, cyclopentene, cyclohexane, cyclohexadiene, cycloheptane, and cycloheptatriene.

The term "$C_{4-9}$ heteroaryl" as used herein and in the claims (unless specified otherwise) means a monocyclic or fused ring (i.e., rings which share an adjacent pair of atoms) group having 4 to 9 carbon atoms and in the ring(s) one or more atoms selected from the group consisting of nitrogen, oxygen and sulfur and, in addition, having a completely conjugated pi-electron system.

The term "$C_{3-10}$ heterocycloalkyl" as used herein and in the claims (unless specified otherwise) means a monocyclic or fused ring (i.e., rings which share an adjacent pair of atoms) group having 3 to 10 carbon atoms and in the ring(s) one or more atoms selected from the group consisting of nitrogen, oxygen and sulfur wherein one or more rings do not have a completely conjugated pi-electron system.

The term "Ph" refers to phenyl or phenylene.

The term "$C_{2-4}$ alkoxy" refers to an —O—$C_{1-4}$ alkyl as defined herein.

The term "$C_{1-4}$ alkyl alcohol" refers to an —ROH group in which R is $C_{1-4}$ alkyl as defined herein.

The term "hydroxy" refers to an —OH group.

The term "halo" refers to chlorine, bromine, iodine or fluorine.

The term "cyano" refers to a —CN group.

The term "thiohydroxy" refers to an —SH group.

The term "amino" refers to an —$NH_2$ group.

The term "carbonyl" refers to a —C(=O)—R group, where R is selected from the group consisting of hydrogen, $C_{1-6}$ alkyl, $C_{2-6}$ alkenyl, $C_{2-6}$ alkynyl, $C_{3-6}$ cycloalkyl, $C_{4-6}$ aryl, and $C_{3-6}$ heteroaryl (bonded through a ring carbon).

The term "sulfonyl" refers to an —S(=O)$_2$R" group with R being $C_{1-6}$ alkyl.

The term "sulfamoyl" refers to an —S(=O)$_2$—$NR_xR_y$ group or a $R_yS(O)_2$—$NR_x$— group or, where $R_x$ and $R_y$ are selected from the group consisting of hydrogen, $C_{1-6}$ alkyl, $C_{2-6}$ alkenyl, $C_{2-6}$ alkynyl, $C_{3-6}$ cycloalkyl, $C_{4-6}$ aryl, and $C_{3-6}$ heteroaryl (bonded through a ring carbon).

The term "carbamoyl" refers to an —OC(=O)$NR_xR_y$ group or $R_xOC(=O)NR_y$— group, with $R^x$ and $R^y$ independently being H or $C_{1-6}$ alkyl.

The term "$C_{1-4}$ haloalkyl" refers to a $C_{1-4}$ alkyl group substituted by at least one halogen atom.

The term "$C_{1-4}$ haloalkylthio" refers to an —SR group where R is $C_{1-4}$ alkyl substituted by at least one halogen atom.

The term "$C_{1-4}$ alkylamino" refers to an —$RNH_2$ group where R is $C_{1-4}$ alkyl.

The term "$C_{1-4}$ alkylsulfonyl" refers to an —S(=O)$_2$R group where R is $C_{1-4}$ alkyl.

The term "$C_{1-4}$ haloalkylsulfonyl" refers to an —S(=O)$_2$R group where R is $C_{1-4}$ alkyl substituted by at least one halogen atom.

The term "$C_{1-4}$ alkoxycarbonyl" refers to a —C(=O)OR group where R is $C_{1-4}$ alkoxy.

The term "$C_{1-4}$ alkxylcarbamoyl" refers to an —OC(=O)$NR_xR_y$ group or $R_xOC(=O)NR_y$— group, group where $R_x$ is $C_{1-4}$ alkyl.

The term "$C_{1-4}$ alkxylcarbamoyl" refers to an —OC(=O)$NR_xR_y$ group or $R_xOC(=O)NR_y$— group, group where $R_x$ is $C_{1-4}$ alkyl.

The term "ureido" refers to an —$NR^xC(=O)NR^yR^z$ group, with $R^x$, $R_y$, and $R^z$ independently being H or $C_{1-6}$ alkyl.

The term "amido" refers to a —C(=O)$NR^xR^y$ or —$R^xC(=O)NR^y$— group, with $R^x$ and $R^y$ independently being H or $C_{1-6}$ alkyl. The term "$C_{1-4}$ alkylamido" refers to amido as defined herein wherein $R_x$ is $C_{1-4}$ alkyl.

Other objects, advantages, and novel features of the invention will become more apparent from the following detailed description when taken in conjunction with the accompanying drawings.

DETAILED DESCRIPTION OF THE PREFERRED EMBODIMENT

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of active 1,2,3-triazole derivatives or an analogue thereof. Examples of other carriers include colloidal silicon oxide, magnesium stearate, cellulose, sodium lauryl sulfate, and D&C Yellow # 10.

To practice the method of the present invention, a composition having one or more of the above-described 1,2,3-triazole derivatives and their analogues can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active 1,2,3-triazole derivatives or their analogues can also be administered in the form of suppositories for rectal administration.

The following exemplifies the synthesis of 1,2,3-triazoles derivatives of the present invention.

EXAMPLE 1

The synthesis of 4,5-diaryl-N1-substituted-1,2,3-triazoles

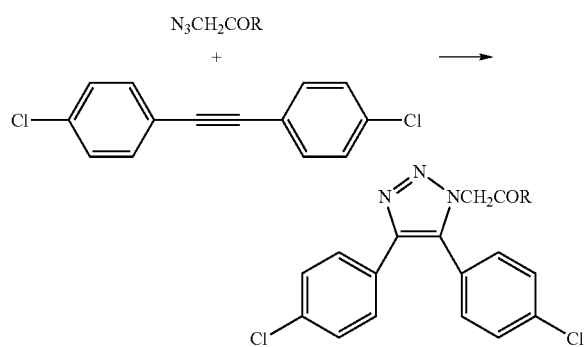

First, as shown in Scheme 1, diaryl acetylenes (such as di-4-chlorophenyl acetylenes) and azides (such as $N_3CH_2COO^nBu$ and $N_3CH_2CON(CH_2)_5$) were added to benzene in the presence of $RuCpCl(PPh_3)_3$, and refluxed to synthesize 4,5-diaryl-N1-substituted-1,2,3-triazoles under Ru-catalyzed cyclization reaction. The yield of the reaction was about from 75% to 80%. Table 1 lists derivatives of 4,5-diaryl-N1-substituted-1,2,3-triazoles, synthesized from different starting materials according to Scheme 1.

In addition, the affinity of test compounds of this invention toward CB1 and CB2 receptors was determined by competitive radioligand binding assays in vitro. This method differentiates the binding strength between compounds by their abilities in displacing a receptor-specific radioactive ligand. Compounds with higher affinity than the radioactive ligand displace the specific radioactive ligand and bind to the receptors, while compounds with no affinity or lower affinity than the radioactive ligand do not. The readings of the radioactivity retained allow further analysis of receptor binding, and assist in predictions of the pharmacological activities of the test compounds.

In the assays, CB1 receptors are from human CB1 stably expressed cell lines, and CB2 receptors are from human CB2 stably expressed cell lines. For purification of membrane-enriched fractions, cells were scraped off from the culture dishes in ice-cold buffer A (50 mM Tris, 5 mM $MgCl_2$, 2.5 mM EDTA, pH 7.4, 10% sucrose) with 1 mM PMSF. After sonication, the membrane-enriched fractions were centrifuged for 15 minutes at 2,000×g at 4° C. The supernatant was centrifuged again for 30 minutes at 43,000×g at 4° C. The final pellet was re-suspended in buffer A and stored at −80° C. The protein concentration of the purified membrane was determined by the Bradford method as described by the manual provided by Bio-Rad Laboratories, Inc., Hercules, Calif.

During the receptor binding experiments, 0.2~8 μg of membrane fractions were incubated with 0.75 nM [$^3$H]CP55,940 and a test compound in the incubation buffer of 50 mM Tris-HCl, 5 mM $MgCl_2$, 1 mM EDTA, 0.3% BSA, pH 7.4. The non-specific binding was determined by using 1 μM of CP55,940. The mixture was incubated for 1.5 hours at 30° C. in Multiscreen microplates (Millipore, Billerica, Mass.). At the completion of the incubation, the reaction was terminated by Manifold filtration and washed with ice-cold wash buffer (50 mM Tris, pH 7.4, 0.25% BSA) four times. The radioactivity bound to the filters was measured by Topcount (Perkin Elmer Inc.). $IC_{50}$ values were calculated based on the concentration of the compounds required to inhibit 50% of the binding of [$^3$H]CP55,940.

The activities of the compounds were determined by DELFIA GTP-binding kit (Perkin Elmer Inc., Boston, Mass.). The DELFIA GTP-binding assay is a time-resolved fluorometric assay based on GDP-GTP exchange on G-protein subunits followed by activation of a G protein-coupled receptor by its agonists. Eu-GTP was used to monitor agonist-dependent activation of G protein. Note that stimulation of CB1 receptors by CP55,940 leads to the replacement of GDP by GTP on the α-subunit of G protein. The resultant GTP-Gα complex represents the activated form of G protein. Eu-GTP, a non-hydrolysable analogue of GTP, is used to quantify the amount of activated G protein (Peltonen et al., Eur. J. Pharmacol. (1998) 355:275).

CB1 containing membrane fraction as described above was diluted in the assay buffer (50 mM HEPES, pH 7.4, 100 mM NaCl, 100 μg/mL saponin, 5 mM $MgCl_2$, 2 μM GDP, 0.5% BSA) and added to the wells of AcroPlates (Pall Life Sciences, Ann Arbor, Mich.). After addition of a test compound (various concentrations in 0.1% DMSO) and CP55,940 (20 nM in the assay buffer), the assay plate was incubated in the dark at 30° C. with slow shaking for 60 minutes. Eu-GTP was added to each well and the plate was incubated for another 35 minutes at 30° C. in the dark. The assay was terminated by washing the plate four times with a wash solution provided in the assay kit. Binding of the Eu-GTP was determined based on the fluorescence signal from a Victor 2 multi-label reader. The $IC_{50}$ value (i.e., 50% inhibition of CP55,940-stimulated Eu-GTP binding) for each test compound was determined by a concentration-response curve using nonlinear regression (Prism; GraphPad, San Diego, Calif.).

The results of the above-mentioned assay are summarized in Table 1.

TABLE 1

| No. | Compound | M.w. | CB1 Inhibition (%) (10 μM)[b] |
|---|---|---|---|
| 1 | 4,5-diphenyl-1H-1,2,3-triazol-1-yl acetic acid butyl ester | 335.40 | 40.8% |
| 2 | N,N-diethyl-2-(4,5-diphenyl-1H-1,2,3-triazol-1-yl)acetamide | 334.41 | 22.6% |
| 3 | 1-(4,5-diphenyl-1H-1,2,3-triazol-1-yl)acetyl piperidine | 346.43 | 26.6% |
| 4 | 4-phenyl-1H-1,2,3-triazol-1-yl acetic acid butyl ester | 259.30 | 9.6% |
| 5 | N,N-diisopropyl-2-(4,5-diphenyl-1H-1,2,3-triazol-1-yl)acetamide | 362.47 | 18.0% |
| 6 | 4,5-bis(3,4-dichlorophenyl)-1H-1,2,3-triazol-1-yl acetic acid butyl ester | 473.18 | 50.5% |
| 7 | N-allyl-2-(4,5-diphenyl-1H-1,2,3-triazol-1-yl)acetamide | 318.37 | 15.4% |

TABLE 1-continued

| No. | Compound | M.w. | CB1 Inhibition (%) (10 μM)[b] |
|---|---|---|---|
| 8 | | 361.44 | 12.3% |
| 9 | | 292.34 | 21.1% |
| 10 | | 482.02 | 20.3% |
| 11 | | 414.10 | 20.4% |
| 12 | | 450.08 | 30.7% |
| 13 | | 259.30 | 22.0% |

TABLE 1-continued

| No. | Compound | M.w. | CB1 Inhibition (%) (10 μM)[b] |
|---|---|---|---|
| 14 | | 404.29 | 64.1% |
| 15 | | 369.42 | 35.4% |
| 16 | | 415.32 | 33.0% |
| 17 | | 484.21 | 25.9% |
| 18 | | 382.41 | 19.7% |
| 19 | | 404.29 | 36.7% |

TABLE 1-continued

| No. | Compound | M.w. | CB1 Inhibition (%) (10 μM)[b] |
|---|---|---|---|
| 20 | | 418.32 | 51.2% |
| 21 | | 440.27 | 15.7% |
| 22 | | 371.38 | 27.1% |
| 23 | | 473.17 | 29.9% |
| 24 | | 349.40 | 31.6% |

TABLE 1-continued

| No. | Compound | M.w. | CB1 Inhibition (%) (10 μM)[b] |
|---|---|---|---|
| 25 | | 446.40 | 53.6% |
| 26 | | 460.40 | 51.2% |
| 27 | | 363.60 | 46.0% |
| 28 | | 432.34 | 36.5% |

TABLE 1-continued

| No. | Compound | M.w. | CB1 Inhibition (%) (10 μM)[b] |
|---|---|---|---|
| 29 | | 393.44 | 31.9% |
| 30 | | 365.43 | 40.0% |
| 31 | | 360.41 | 18.9% |
| 32 | | 390.26 | 28.3% |

TABLE 1-continued

| No. | Compound | M.w. | CB1 Inhibition (%) (10 μM)[b] |
|---|---|---|---|
| 33 | | 418.32 | 24.6% |
| 34 | | 395.45 | 45.9% |
| 35 | | 471.40 | 46.00% |
| 36 | | 369.84 | 35.20% |

TABLE 1-continued

| No. | Compound | M.w. | CB1 Inhibition (%) (10 μM)[b] |
|---|---|---|---|
| 37 | | 349.43 | 26.50% |
| 38 | | 390.52 | 23.80% |
| 39 | | 502.73 | 4.10% |
| 40 | | 403.40 | 16.30% |

TABLE 1-continued

| No. | Compound | M.w. | CB1 Inhibition (%) (10 μM)[b] |
|---|---|---|---|
| 41 | | 380.40 | 14.70% |
| 42 | | 341.43 | 35.60% |
| 43 | | 360.45 | 34.40% |
| 44 | | 393.44 | 14.10% |
| 45 | | 489.40 | 9.80% |

TABLE 1-continued

| No. | Compound | M.w. | CB1 Inhibition (%) (10 μM)[b] |
|---|---|---|---|
| 46 | | 438.70 | 50.80% |
| 47 | | 449.80 | 61.80% |
| 48 | | 353.40 | 36.10% |
| 49 | | 517.50 | 30.30% |

TABLE 1-continued

| No. | Compound | M.w. | CB1 Inhibition (%) (10 μM)[b] |
|---|---|---|---|
| 50 | | 503.40 | 27.50% |
| 51 | | 475.40 | 18.60% |
| 52 | | 364.40 | 11.00% |
| 53 | | 493.19 | 68.70% |
| 54 | | 473.18 | 71.7% (>10 uM) |

TABLE 1-continued

| No. | Compound | M.w. | CB1 Inhibition (%) (10 μM)[b] |
|---|---|---|---|
| 55 | | 466.79 | 45.70% |
| 56 | | 466.79 | 47.70% |
| 57 | | 501.23 | 55.70% |
| 58 | | 487.21 | 58.30% |
| 59 | | 515.26 | 30.10% |

TABLE 1-continued

| No. | Compound | M.w. | CB1 Inhibition (%) (10 μM)[b] |
|---|---|---|---|
| 60 | | 484.21 | 55.70% |
| 61 | | 451.47 | 46.10% |
| 62 | | 493.19 | 18.30% |
| 63 | | 363.45 | 9.90% |

TABLE 1-continued

| No. | Compound | M.w. | CB1 Inhibition (%) (10 μM)[b] |
|---|---|---|---|
| 64 | | 486.18 | 26.00% |

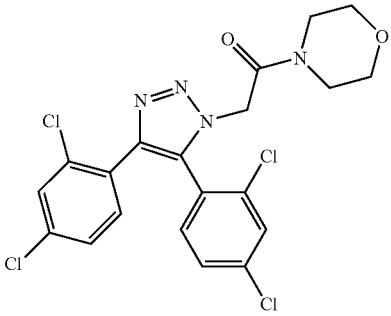

[a]Displacement of specific [³H]-CP55940 binding in HEK 293 cells stably transfected with human CB1 receptor.
[b]Percent inhibition at 10 μM.

EXAMPLE 2

The synthesis of 4,5-diaryl-N2-substituted-1,2,3-triazoles

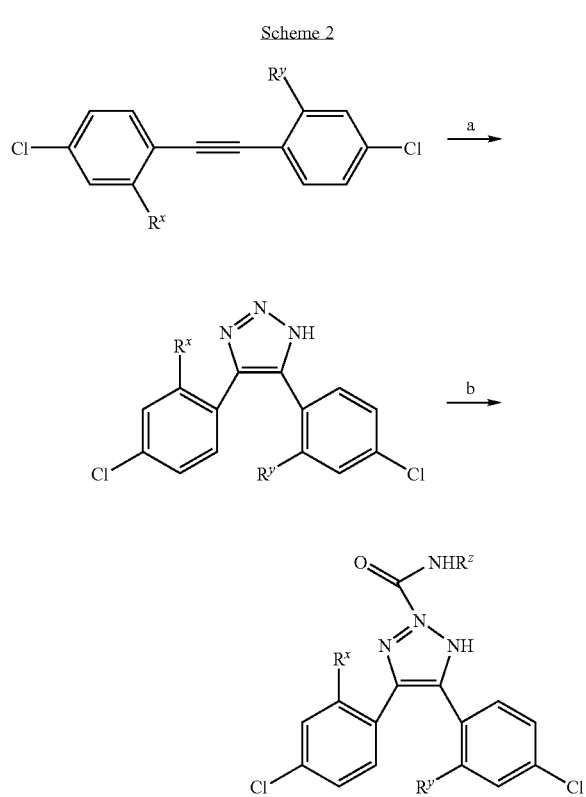

First, as shown in the following Scheme 2, diarylacetylenes were reacted with sodium azide (a) in DMF at 170° C. for 3 to 4 hours to perform 1,3-dipolar cycloaddition reactions. The yield of the reaction was approximately from 75% to 88%. Subsequently, the resultant products, 4,5-diaryl-1,2,3-triazoles, of the abovementioned reaction and various isocyanates (b) (generating ureas) were added in THF in the presence of DMAP, and then refluxed for 1 to 2 hours to perform coupling reactions. The yield of the reaction was around from 20% to 90%.

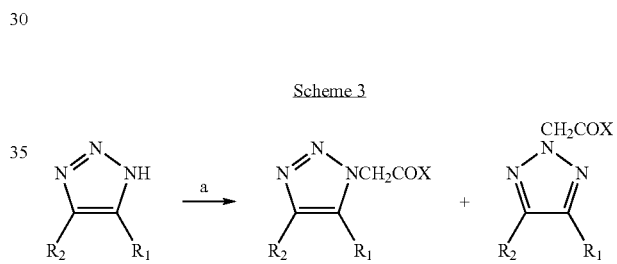

Alternatively, 4,5-diaryl-1,2,3-triazoles (for example 4,5-di-2,4-dichlorophenyl-1,2,3-triazole) were reacted with bromoacetate (such as $BrCH_2CO_2{}^nBu$) or bromoacetamide (such as $BrCH_2CON(CH_2)_5$) by alkylation in THF in the presence of NaH and $Bu_4NI$ at room temperature for 1 hour, resulting in the mixture of 1-substituted and 2-substituted triazoles as shown in Scheme 3. Subsequently, 1- and 2-substituted triazoles were separated by column chromatography and then unmistakably identified by $^1H$ and $^{13}C$ NMR spectroscopy. The results showed that the ratio of 1- and 2-substituted triazoles was about 1/4 to 1/5, and the yield thereof was around from 63% to 66%.

Then, such 2-substituted triazoles (for example 2-(phenoxycarbonyl)methyl triazoles) as convenient precursors were further reacted with amines in toluene, and refluxed for 4 to 12 hours to synthesize amide derivatives of 2-substituted triazoles. The yield of the resulting products was approximately from 65% to 98%.

Table 2 lists derivatives of 4,5-diaryl-N2-substituted-1,2,3-triazoles, synthesized from different starting materials according to Schemes 2 and 3. Besides, the compounds listed in Table 2 were tested under the displacement ligand binding assay as described in Example 1, in comparison with SR141716A. The results of the assay are also summarized in Table 2.

TABLE 2

| No. | Compound |
|---|---|
| 65 | 4,5-diphenyl-2H-1,2,3-triazol-2-yl phenyl ketone |
| 66 | 1-(4,5-diphenyl-2H-1,2,3-triazol-2-yl)-2,2-dimethylpropan-1-one |
| 67 | (2-chlorophenyl)(4,5-diphenyl-2H-1,2,3-triazol-2-yl)methanone |
| 68 | 1-(4,5-bis(2,4-dichlorophenyl)-2H-1,2,3-triazol-2-yl)-2,2-dimethylpropan-1-one |
| 69 | 4,5-bis(4-chlorophenyl)-N-(4-methoxyphenyl)-2H-1,2,3-triazole-2-carboxamide |
| 70 | (4,5-bis(4-chlorophenyl)-2H-1,2,3-triazol-2-yl)(phenyl)methanone |

TABLE 2-continued
| 71 | 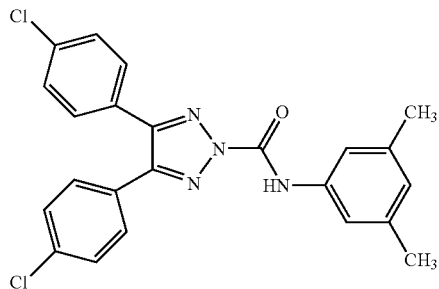 |
| --- | --- |
| 72 | 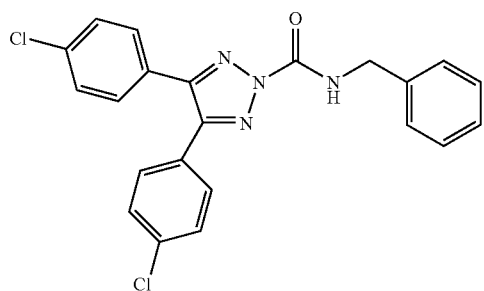 |
| 73 | 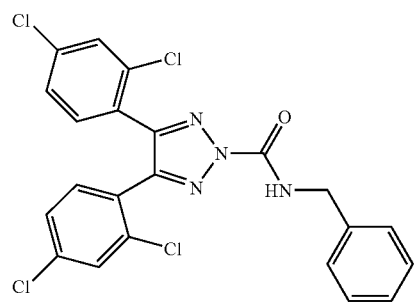 |
| 74 | 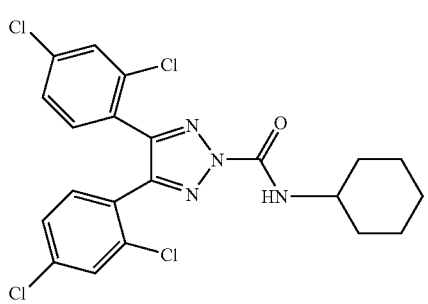 |
| 75 | 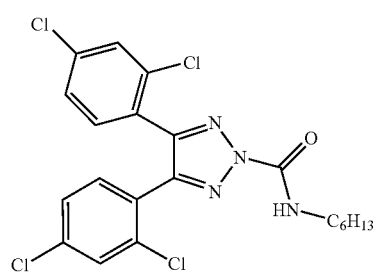 |

TABLE 2-continued
76 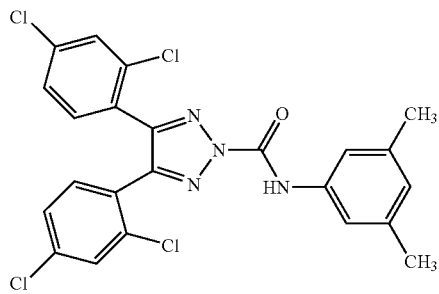
77 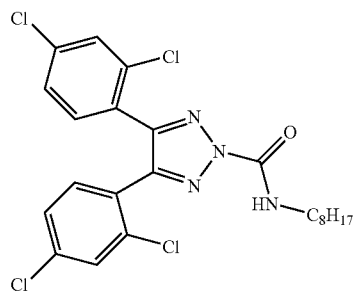
78 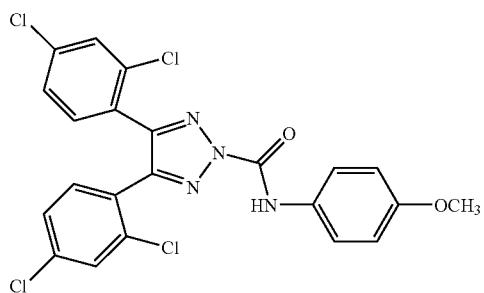
79 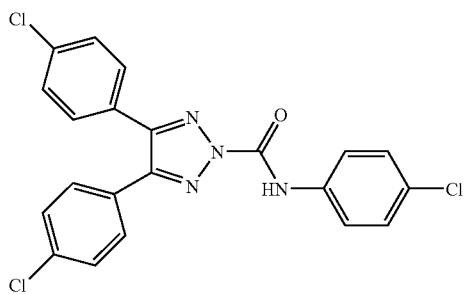
80 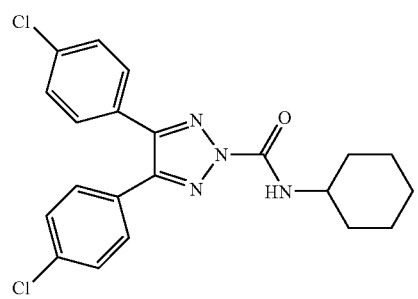

TABLE 2-continued
| | |
|---|---|
| 81 | 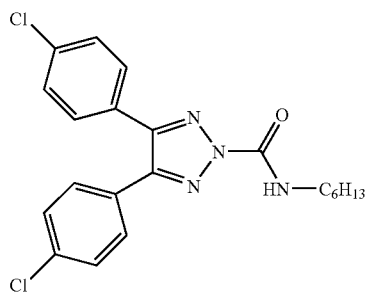 |
| 82 | 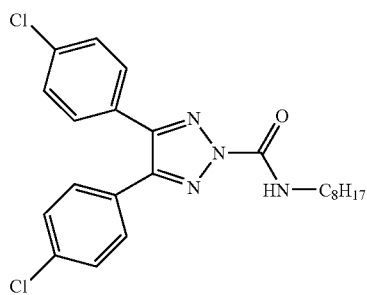 |
| 83 | 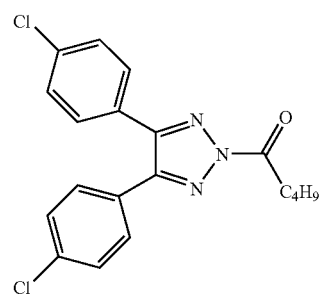 |
| 84 | 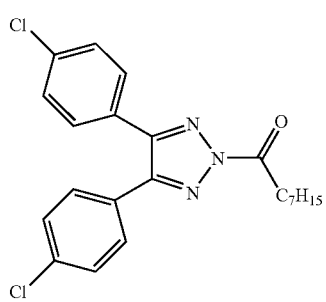 |
| 85 | 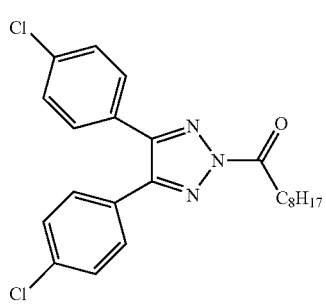 |

TABLE 2-continued
| 86 | 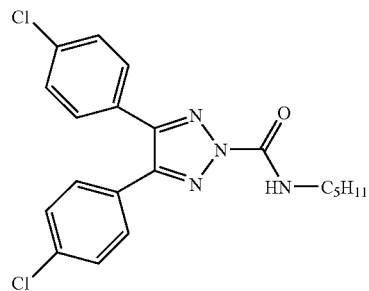 |
| 87 | 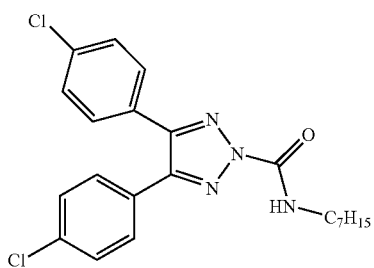 |
| 88 | 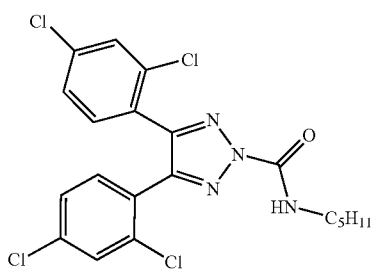 |
| 89 | 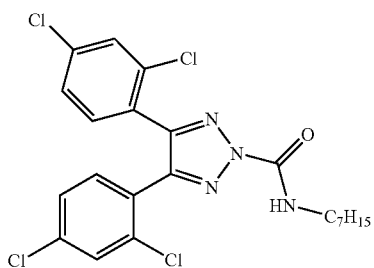 |
| 90 | 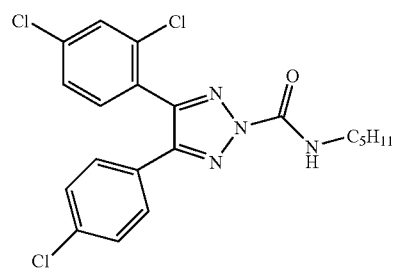 |
| 91 | 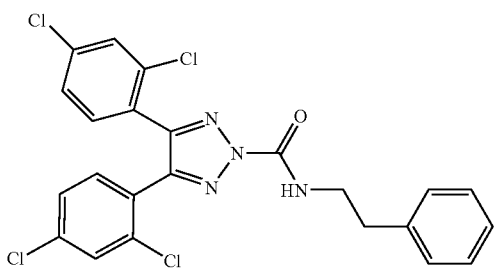 |

TABLE 2-continued
92 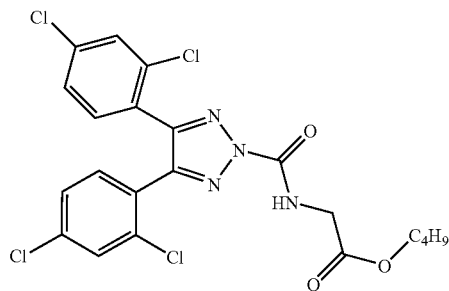
93 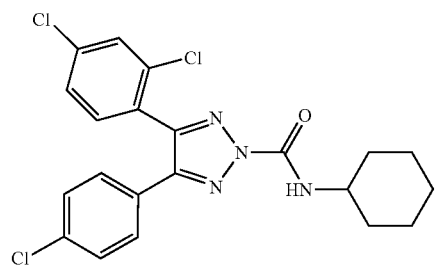
94 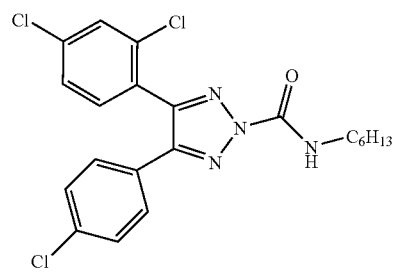
95 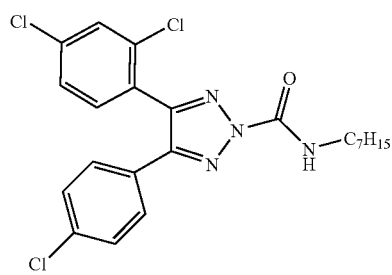
96 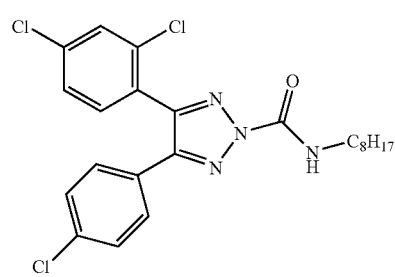

TABLE 2-continued
| 97 | 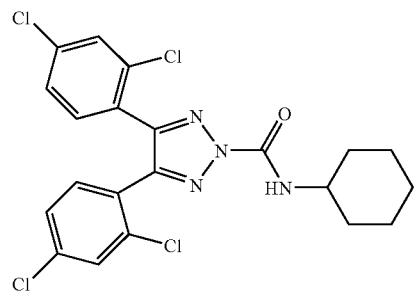 |
| --- | --- |
| 98 | 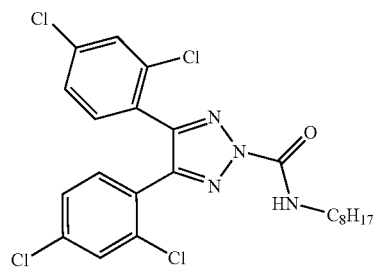 |
| 99 | 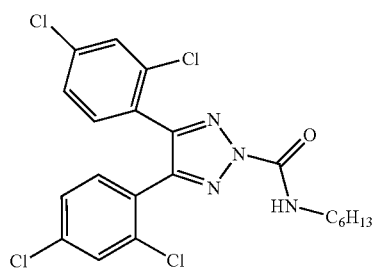 |
| 100 | 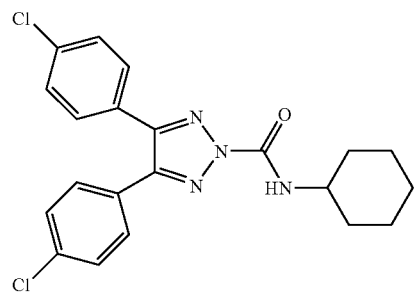 |
| 101 | 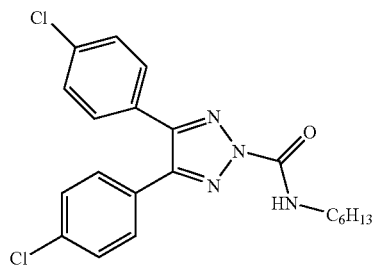 |

TABLE 2-continued
102 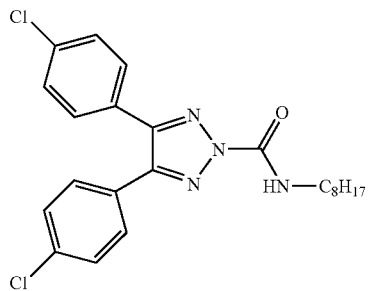
103 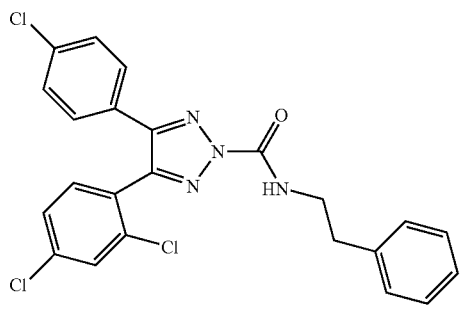
104 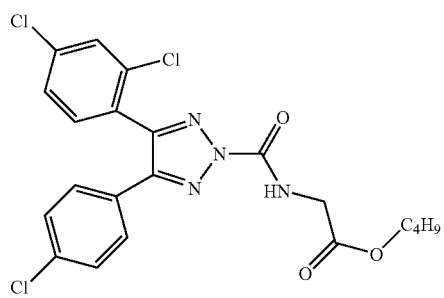
105 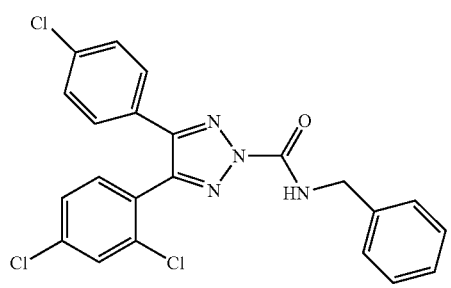
106 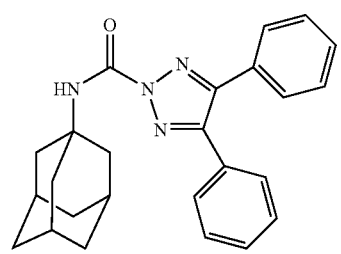

TABLE 2-continued
107 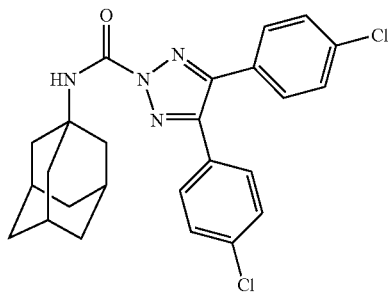
108 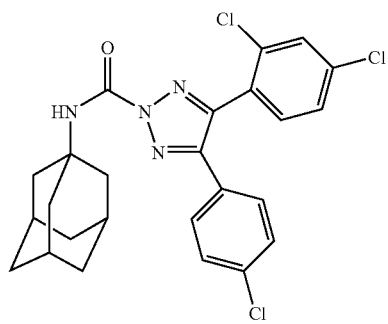
109 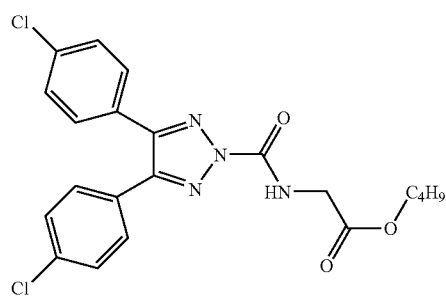
110 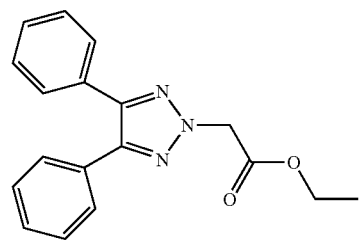
111 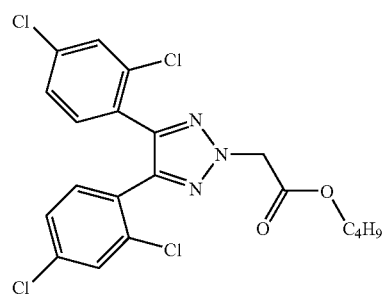

TABLE 2-continued
| | | |
|---|---|---|
| 112 | 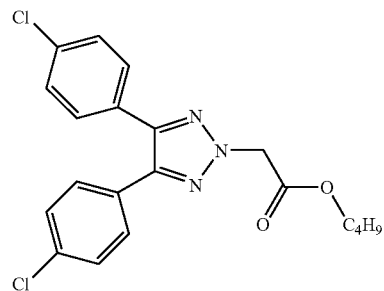 | |
| 113 | 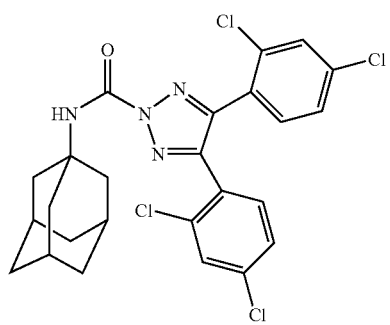 | |
| 114 | 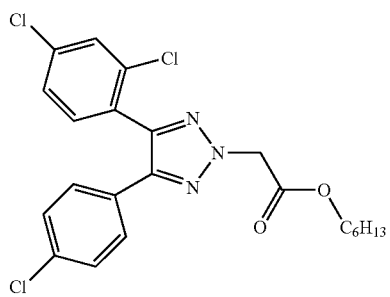 | |
| 115 | 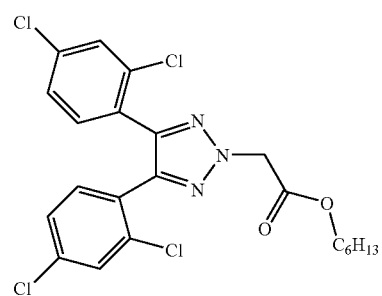 | |
| 116 | 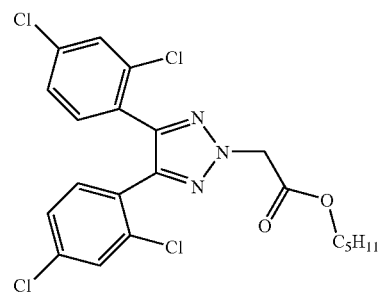 | |

TABLE 2-continued
| 117 | 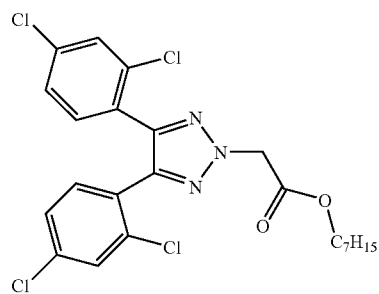 |
| --- | --- |
| 118 | 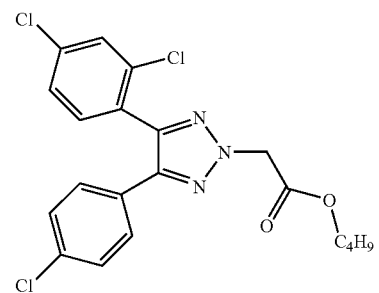 |
| 119 | 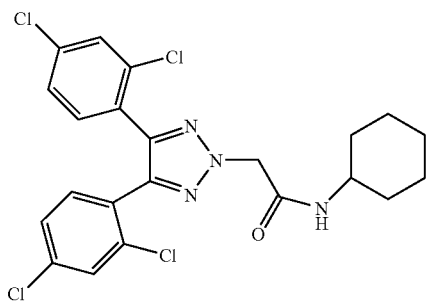 |
| 120 | 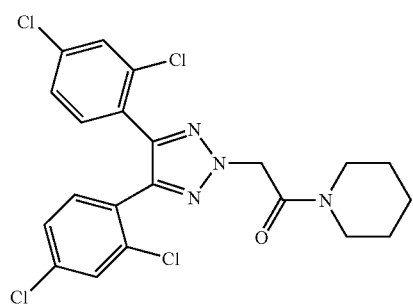 |
| 121 | 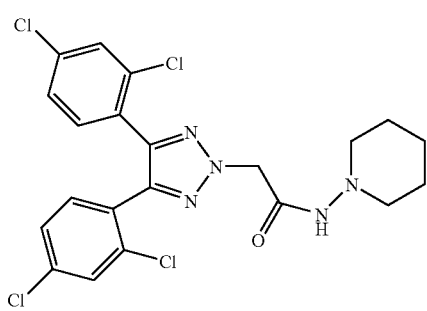 |

TABLE 2-continued
| 122 | 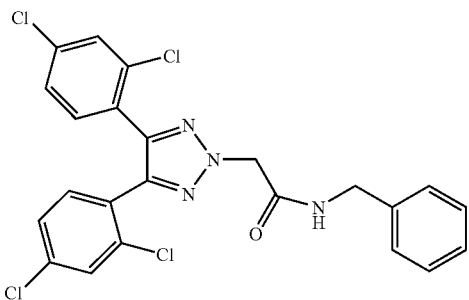 |
| 123 | 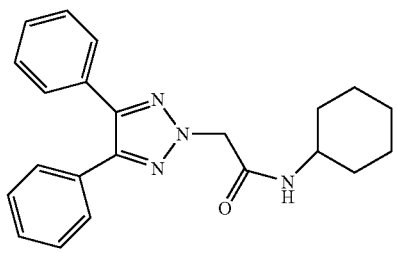 |
| 124 | 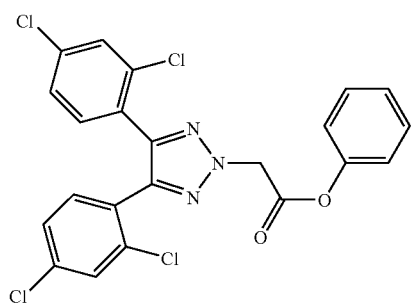 |
| 125 | 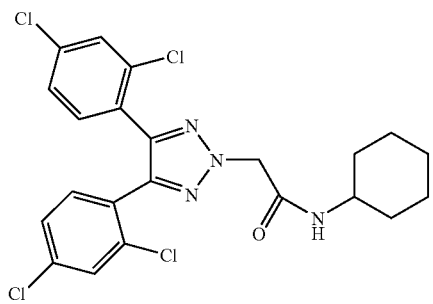 |
| 126 | 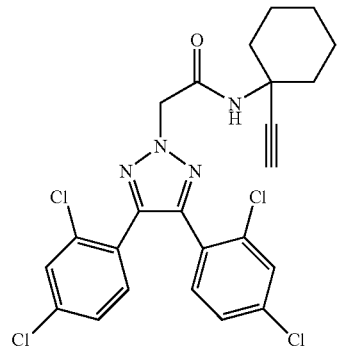 |

TABLE 2-continued
127
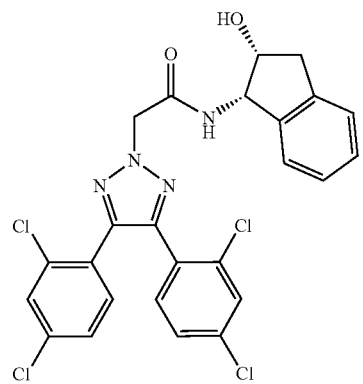
128
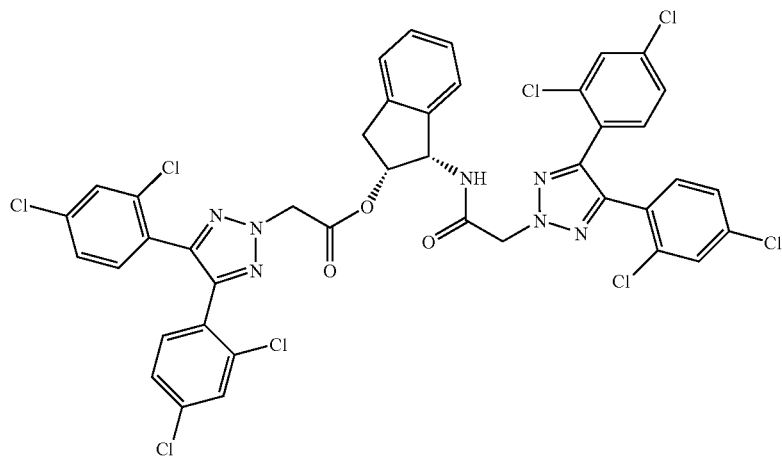
129
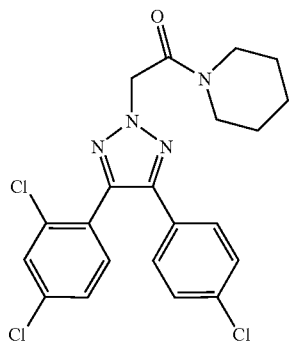
130
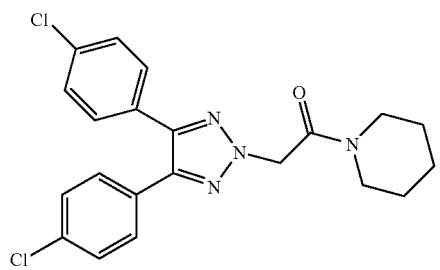

TABLE 2-continued
131
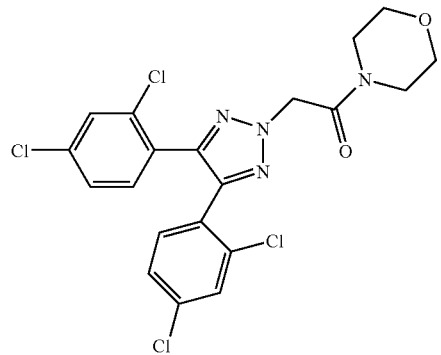
132
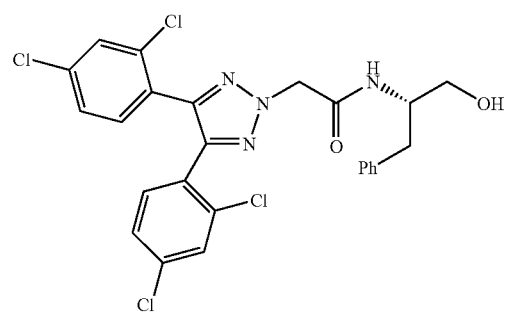
133
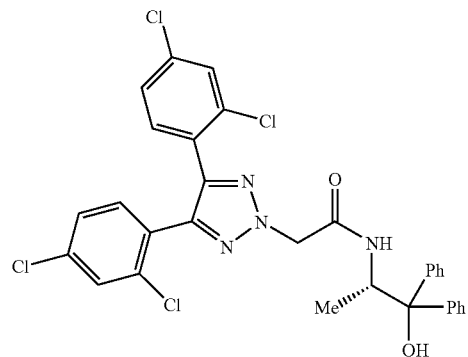
134
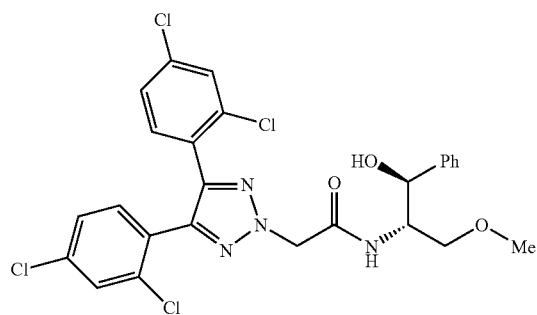

TABLE 2-continued
135
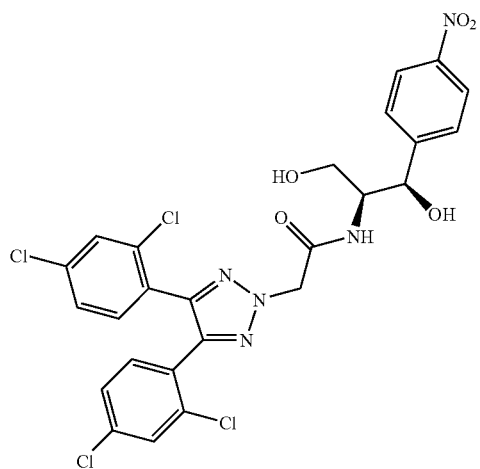
136
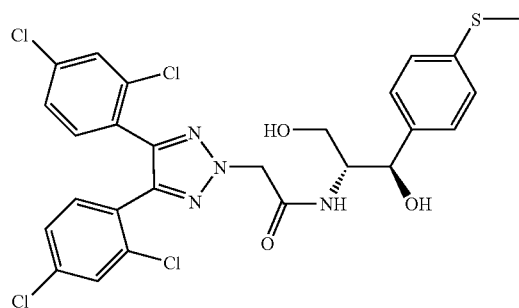
137
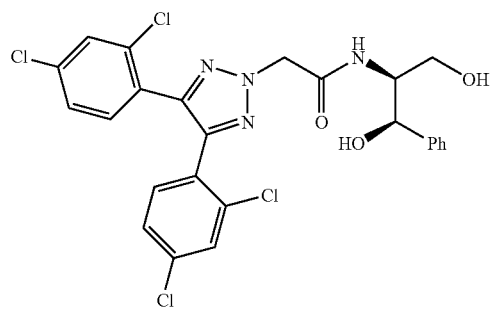
138
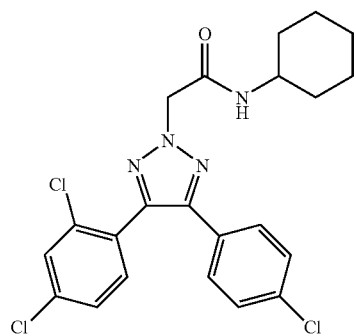

TABLE 2-continued
| 139 | 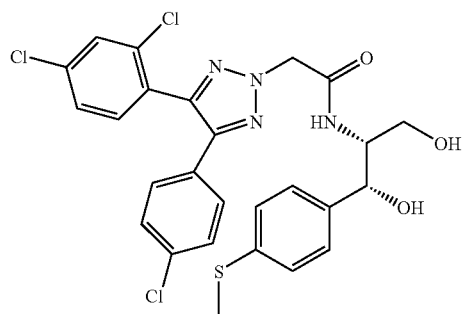 |
| 140 | 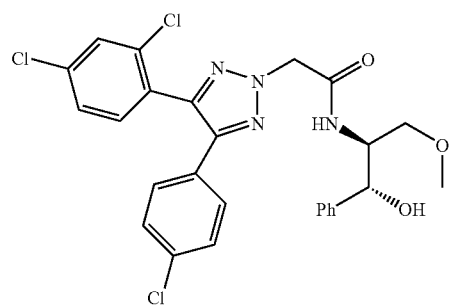 |
| 141 | 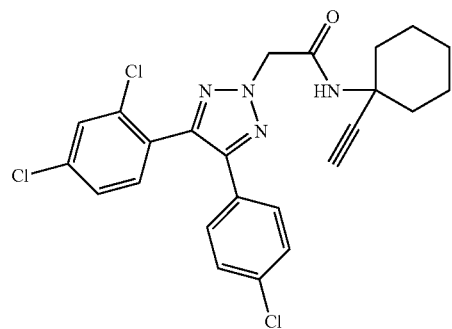 |
| 142 | 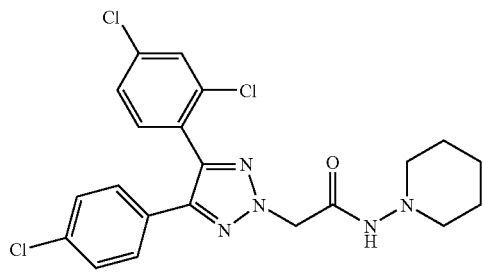 |
| 143 | 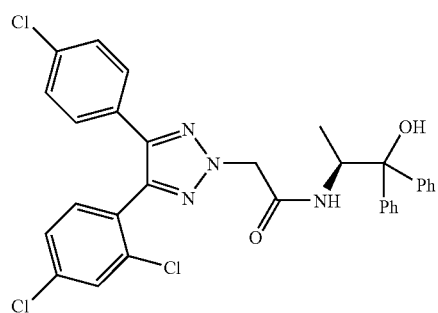 |

TABLE 2-continued
| | |
|---|---|
| 144 | 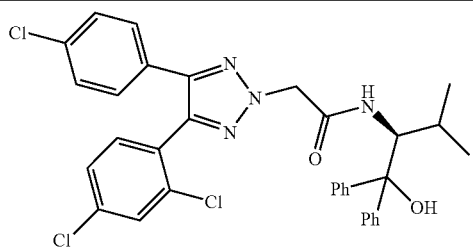 |
| 145 | 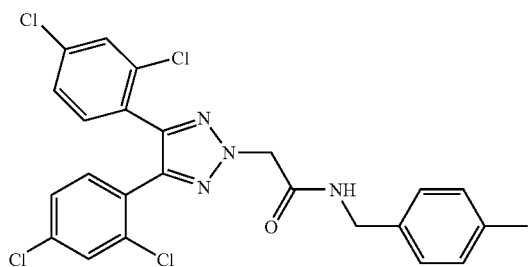 |
| 146 | 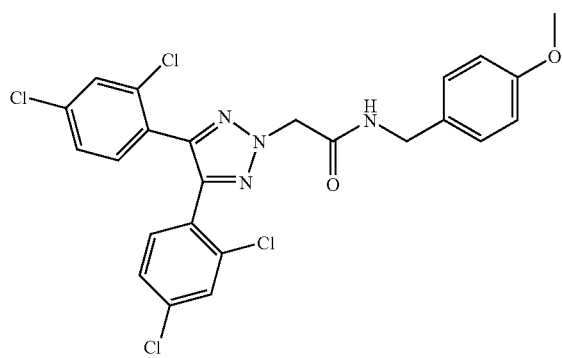 |
| 147 | 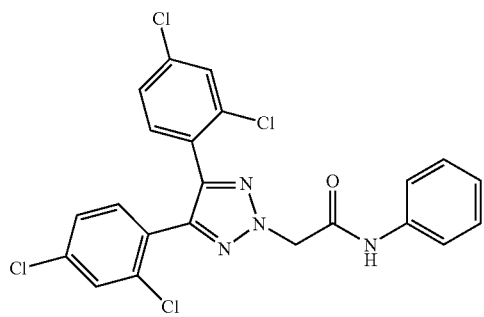 |
| 148 | 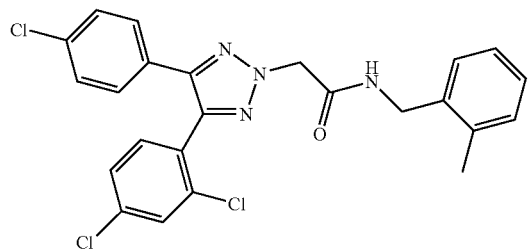 |

TABLE 2-continued
| 149 | 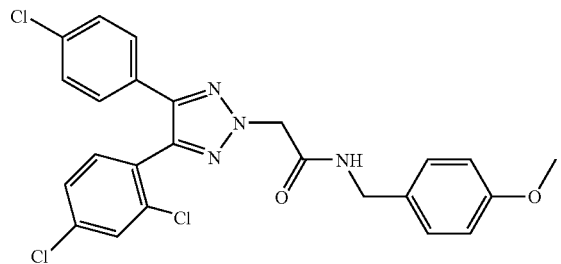 |
| --- | --- |
| 150 | 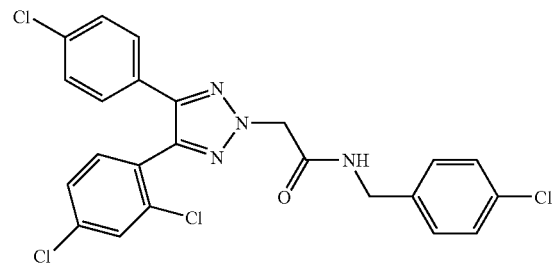 |
| 151 | 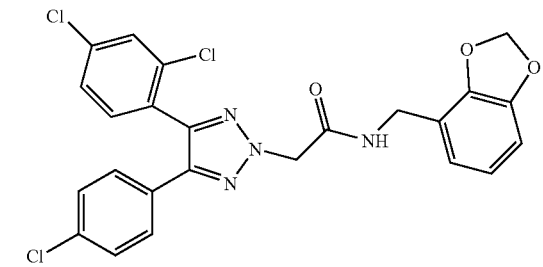 |
| 152 | 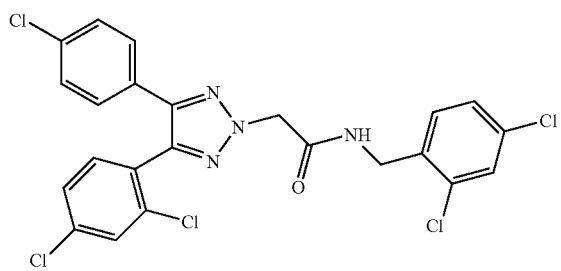 |
| 153 | 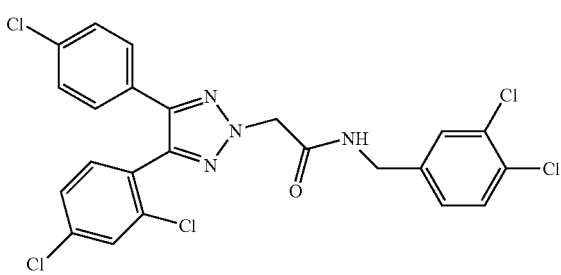 |
| 154 | 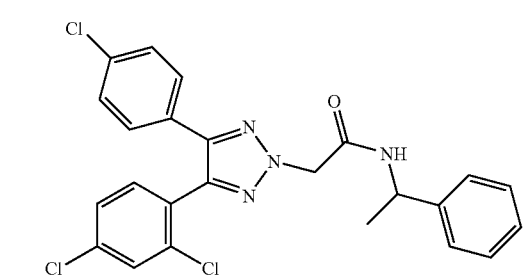 |

TABLE 2-continued
| 155 | 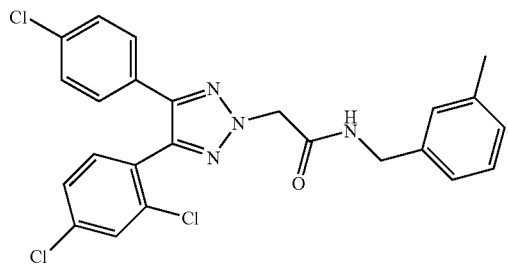 |
| 156 | 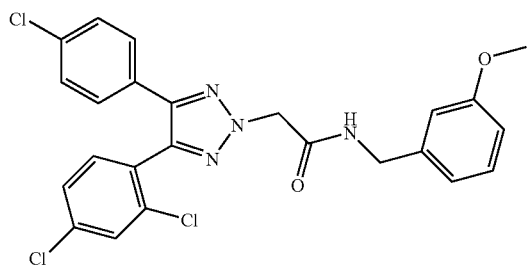 |
| 157 | 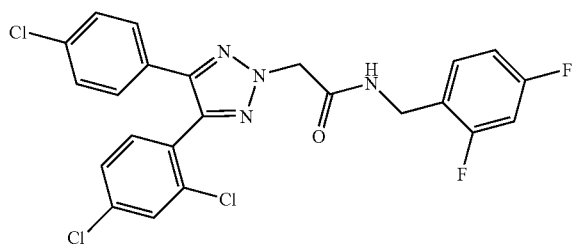 |
| 158 | 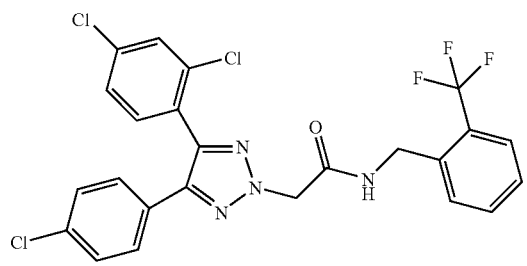 |
| 159 | 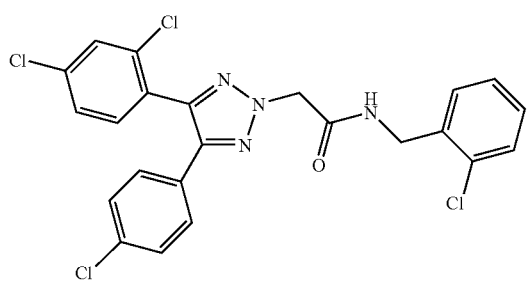 |

TABLE 2-continued
| | |
|---|---|
| 160 | 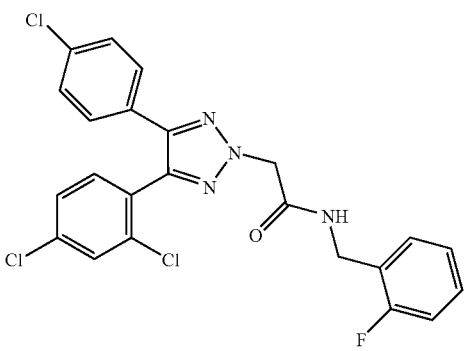 |
| 161 | 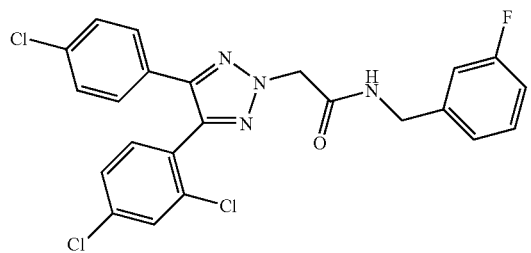 |
| 162 | 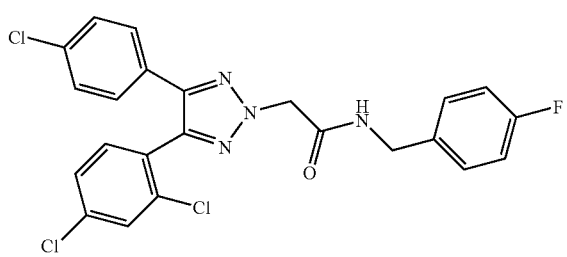 |
| 163 | 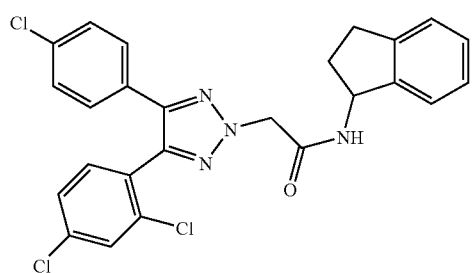 |
| 164 | 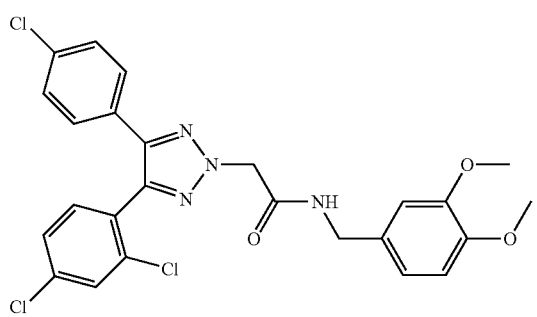 |

TABLE 2-continued
165 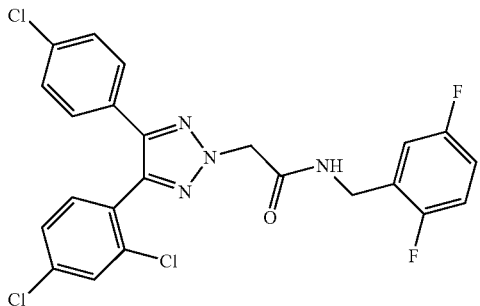
166 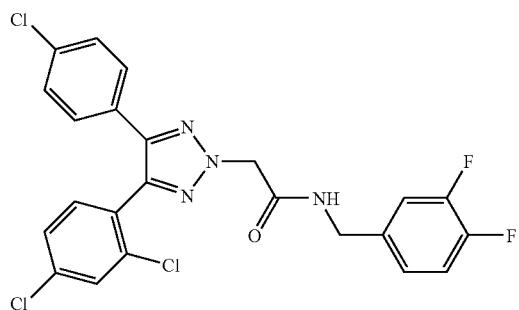
167 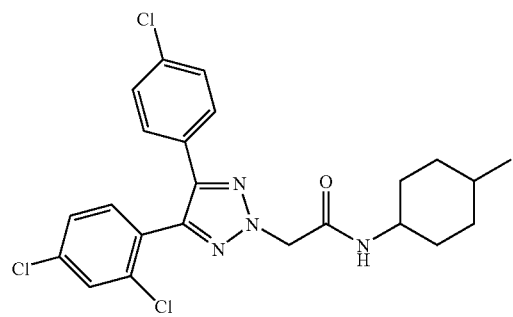
168 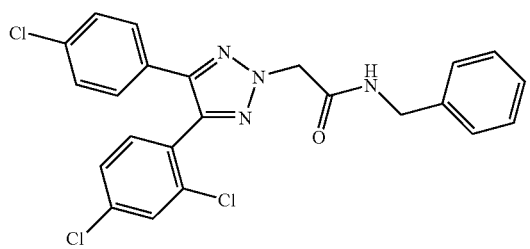
169 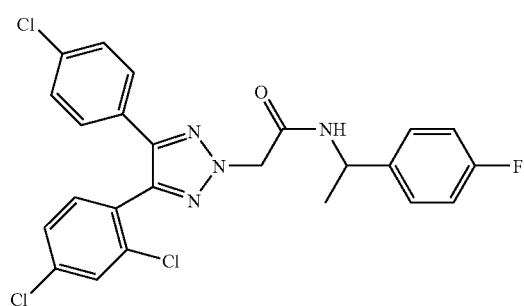

TABLE 2-continued
| 170 | 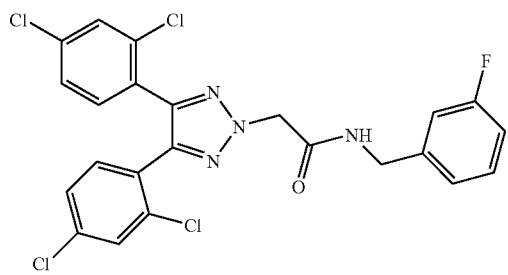 |
| --- | --- |
| 171 | 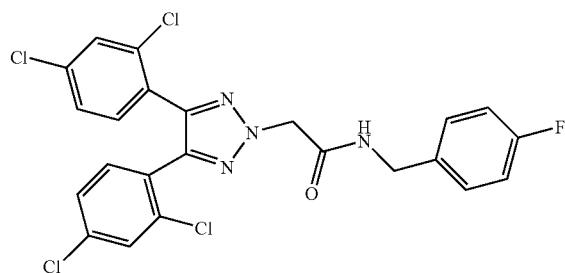 |
| 172 | 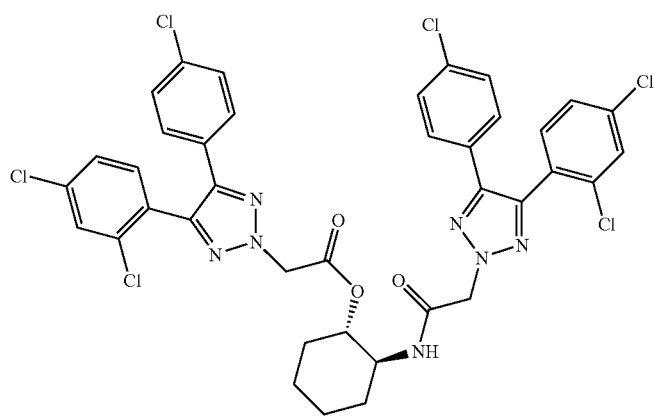 |
| 173 | 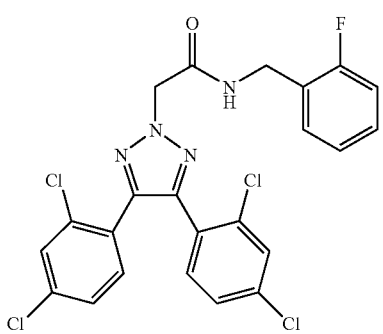 |
| 174 | 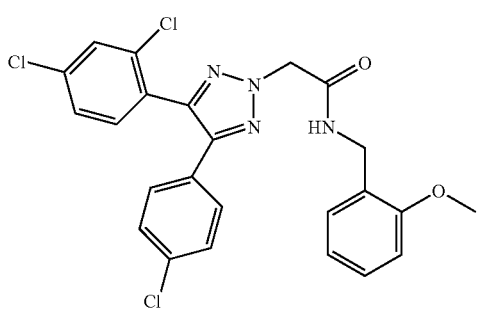 |

TABLE 2-continued
| | |
|---|---|
| 175 | 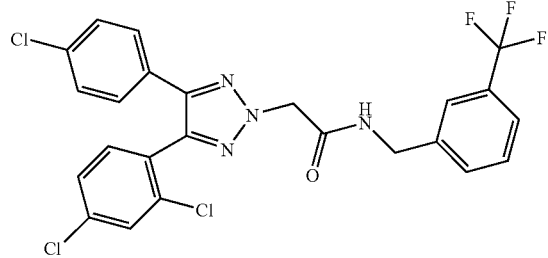 |
| 176 | 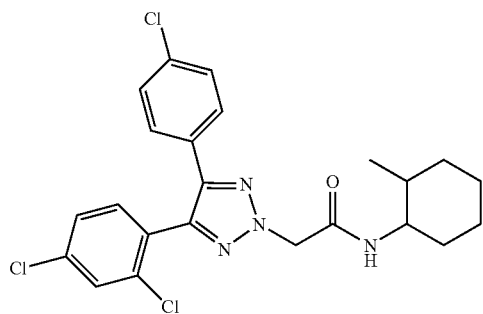 |
| 177 | 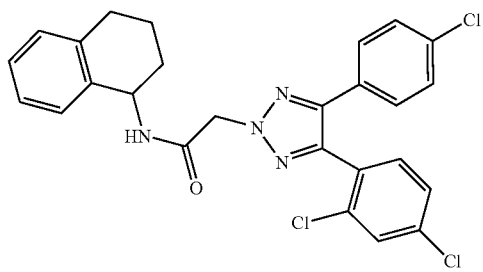 |
| 178 | 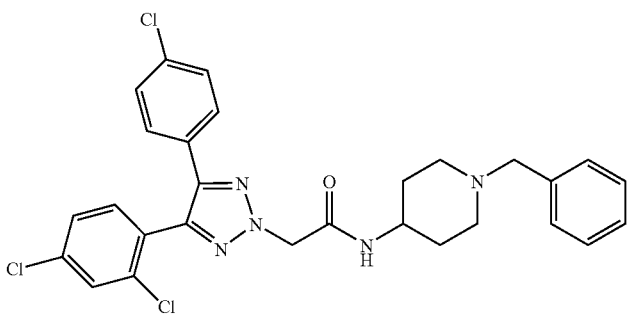 |
| 179 | 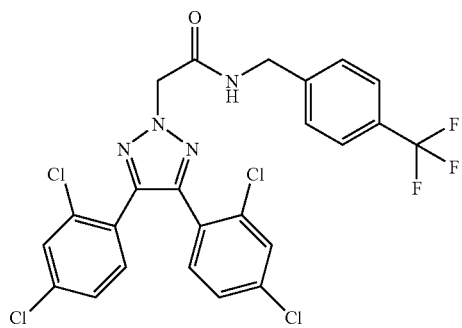 |

TABLE 2-continued
180 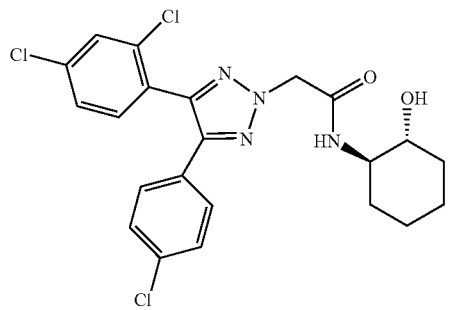
181 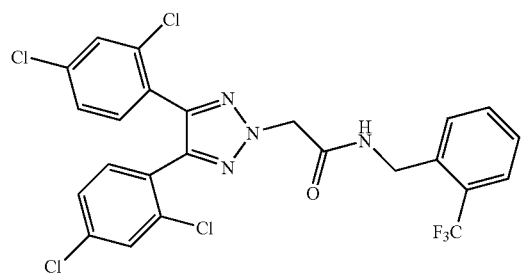
182 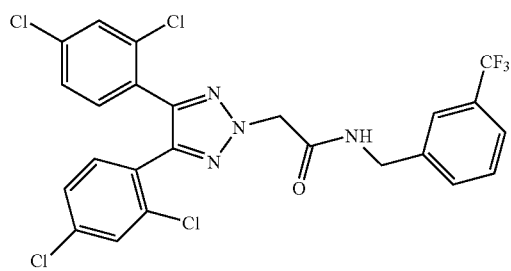
183 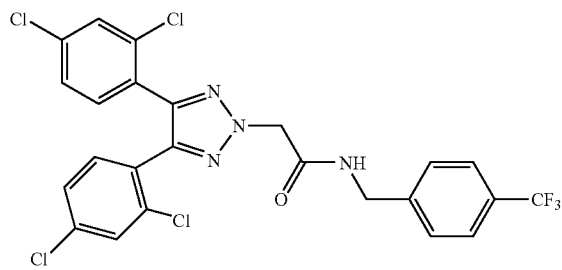
184 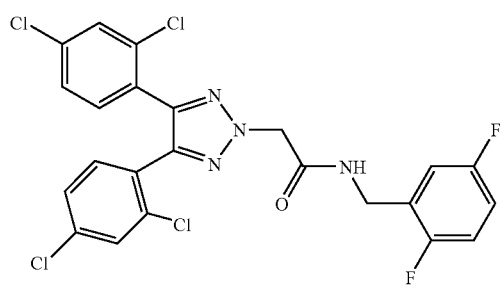

TABLE 2-continued
185 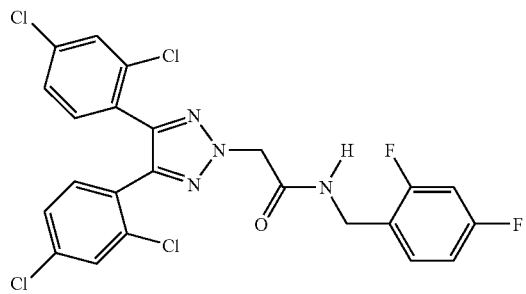
186 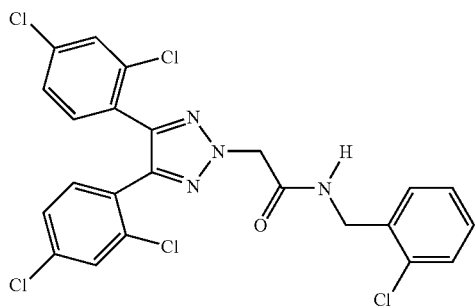
187 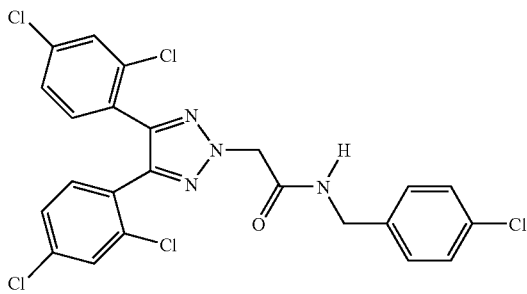
188 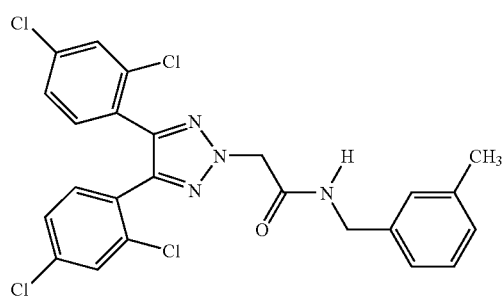
189 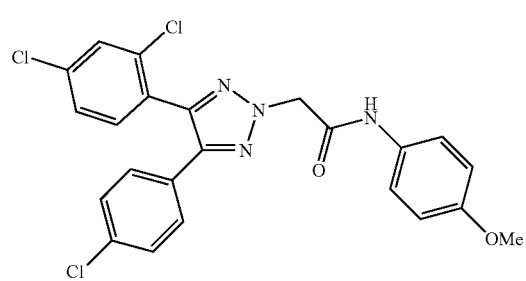

TABLE 2-continued
190 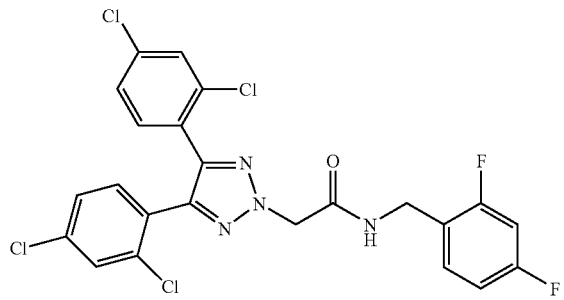
191 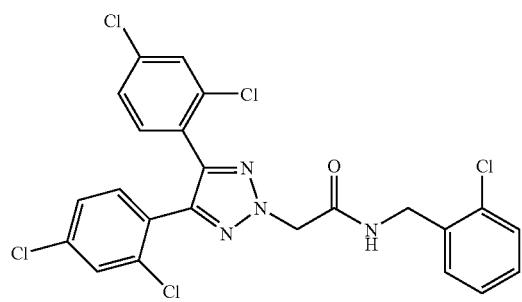
192 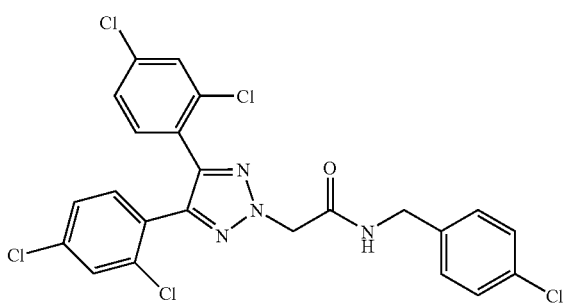
193 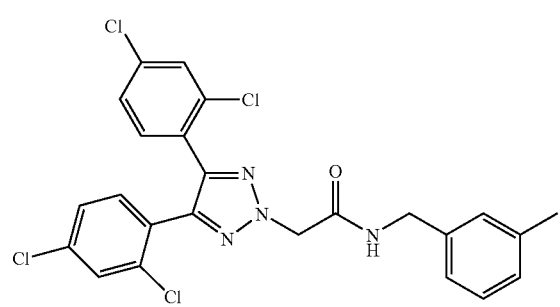
194 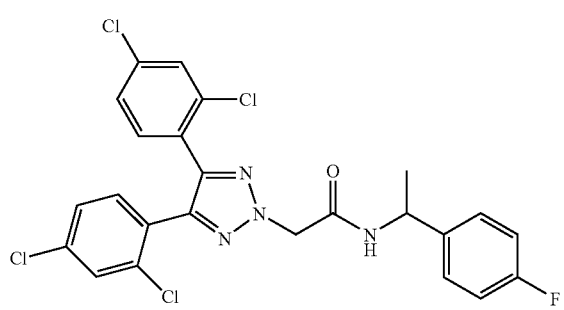

TABLE 2-continued
195 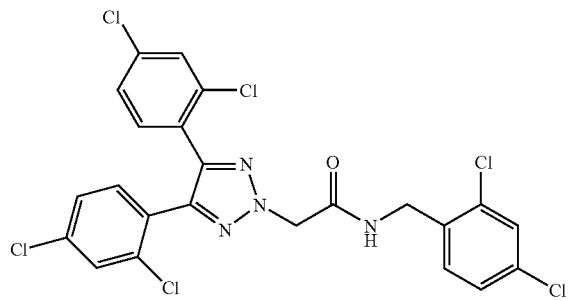
196 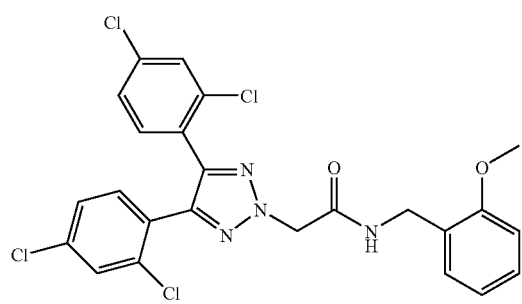
197 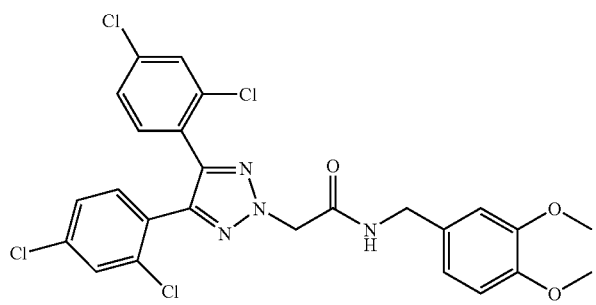
198 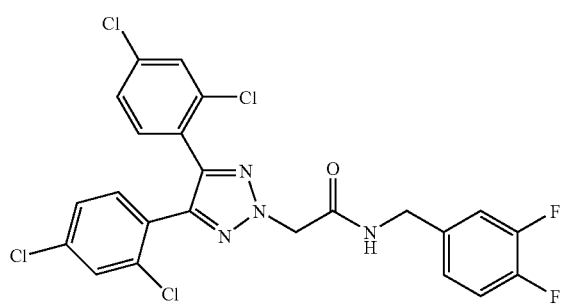
199 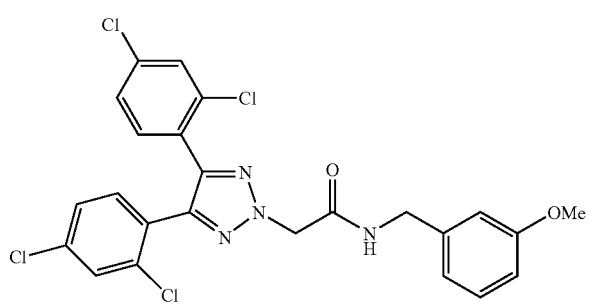

TABLE 2-continued
200 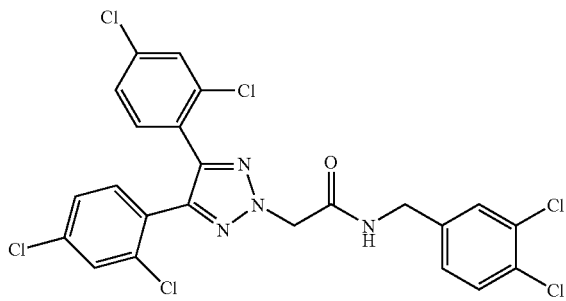
201 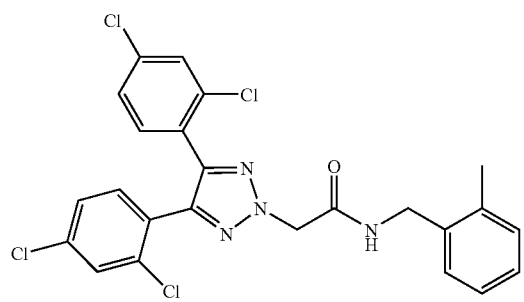
202 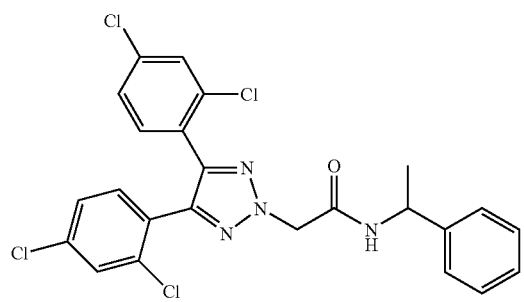
203 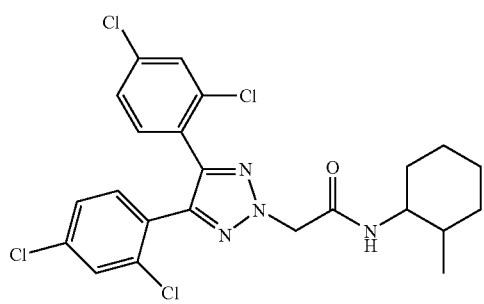
204 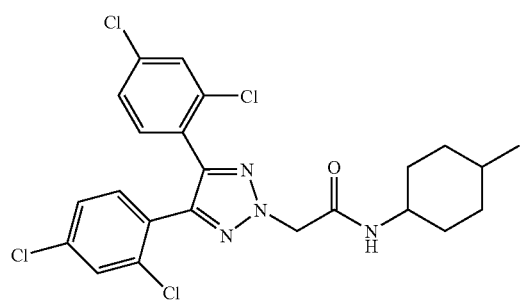

TABLE 2-continued
205 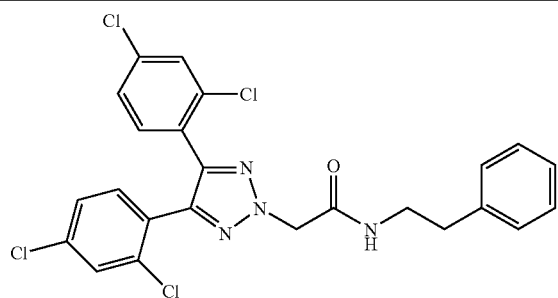
206 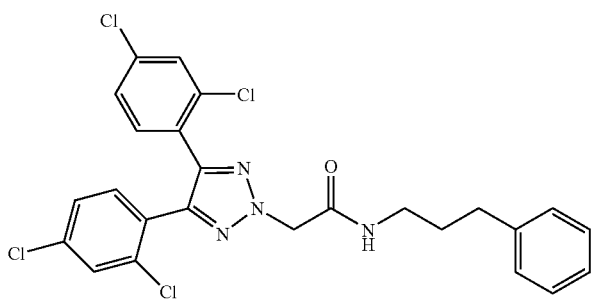
207 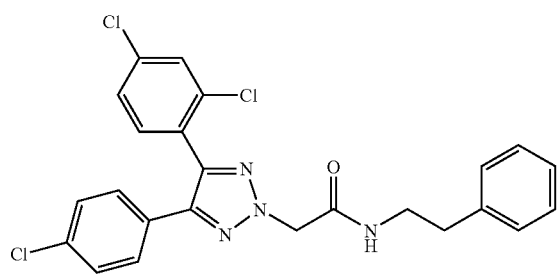
208 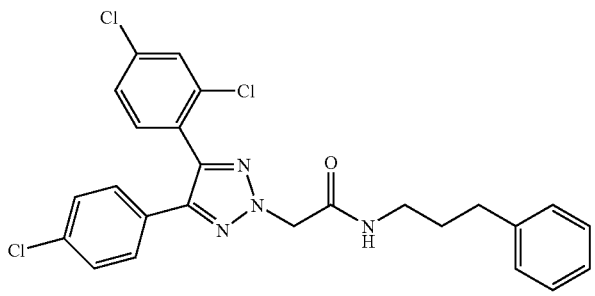
SR141716A
| No. | M.w. | CB1 Inhibition (%) (10 μM)[b] | CB1 IC50 (nM)[a] | CB1 EC50 (nM)[c] | CB2 IC50 (nM) |
|---|---|---|---|---|---|
| 65 | 325.36 | 11.4 | | | |
| 66 | 305.37 | 32.1 | | | |
| 67 | 359.81 | 13.1 | | | |
| 68 | 443.20 | 24.2 | | | |
| 69 | 439.30 | 9.9 | | | |
| 70 | 394.25 | 16.2 | | | |
| 71 | 437.32 | 3.6 | | | |
| 72 | 423.30 | | | | |
| 73 | 492.18 | 23.80 | | | |
| 74 | 484.21 | 50.80 | | | |
| 75 | 514.28 | 3.30 | | | |
| 76 | 506.21 | 12.70 | | | |
| 77 | 486.22 | 27.50 | | | |
| 78 | 508.18 | 6.40 | | | |
| 79 | 443.71 | 1.50 | | | |
| 80 | 415.32 | 29.90 | | | |

TABLE 2-continued

| # | MW | % | | | |
|---|---|---|---|---|---|
| 81 | 417.33 | 41.50 | | | |
| 82 | 445.38 | 26.90 | | | |
| 83 | 374.26 | 11.80 | | | |
| 84 | 416.34 | 21.20 | | | |
| 85 | 430.37 | 18.30 | | | |
| 86 | 403.31 | 8.40 | | | |
| 87 | 431.36 | 12.90 | | | |
| 88 | 472.20 | 7.00 | | | |
| 89 | 500.25 | 12.90 | | | |
| 90 | 437.75 | 14.40 | | | |
| 91 | 506.21 | 11.20 | | | |
| 92 | 516.20 | 22.30 | | | |
| 93 | 449.76 | 30.50 | | | |
| 94 | 451.78 | 10.90 | | | |
| 95 | 465.80 | 14.90 | | | |
| 96 | 479.83 | 17.70 | | | |
| 97 | 484.21 | 29.20 | | | |
| 98 | 514.27 | 19.40 | | | |
| 99 | 486.22 | 6.60 | | | |
| 100 | 415.32 | 19.90 | | | |
| 101 | 417.33 | | | | |
| 102 | 445.38 | 15.70 | | | |
| 103 | 471.77 | 23.40 | | | |
| 104 | 481.76 | 11.80 | | | |
| 105 | 457.74 | 18.60 | | | |
| 106 | 398.50 | 4.80 | | | |
| 107 | 467.39 | 19.70 | | | |
| 108 | 501.84 | 34.50 | | | |
| 109 | 447.31 | 58.10 | | | |
| 110 | 307.35 | 59.10 | | | |
| 111 | 473.18 | 90.30 | 1173.2 ± 263.4 | 486.4 ± 101.6 | >10 μM |
| 112 | 404.29 | 82.10 | 2806.3 ± 300.9 | | |
| 113 | 536.28 | 78.90 | 4496.8 ± 871.1 | | |
| 114 | 466.79 | 39.10 | | | |
| 115 | 501.23 | 72.70 | 4456.3 ± 698.0 | | |
| 116 | 487.21 | 76.50 | 2795.9 ± 544.4 | | |
| 117 | 515.26 | 47.50 | | | |
| 118 | 438.73 | 67.40 | | | |
| 119 | 498.23 | 74.20 | | | |
| 120 | 484.21 | 93.70 | 168.9 ± 32.2 | 122.0 ± 32.1 | 5903.4 ± 763.5 |
| 121 | 499.22 | 70.30 | | | |
| 122 | 506.21 | 99.30 | 66.9 ± 8.9 | 87.0 ± 17.0 | >10 μM |
| 123 | 360.45 | 11.60 | | | |
| 124 | 493.17 | 14.30 | | | |
| 125 | 498.23 | 91.40 | 144.4 ± 110.0 | 203.6 ± 112.3 | >10 μM |
| 126 | 522.25 | 102.30 | 86.8 ± 1.0 | 210.1 ± 77.3 | |
| 127 | 548.25 | 89.40 | 1243.8 ± 697.3 | | |
| 128 | 947.31 | 13.60 | | | |
| 129 | 449.76 | 76.50 | 587.2 ± 139.2 | 185.0 ± 44.5 | |
| 130 | 415.32 | 48.60 | | | |
| 131 | 486.18 | 84.20 | 71.9 ± 16.5 | 143.2 ± 26.8 | |
| 132 | 550.26 | 88.20 | 294.9 ± 111.8 | 753.7 ± 130.6 | |
| 133 | 626.36 | 75.70 | 759.6 ± 273.3 | | |
| 134 | 580.29 | 95.90 | 806.2 ± 346.3 | 223.1 ± 56.4 | |
| 135 | 611.26 | 60.10 | | | |
| 136 | 612.35 | 66.30 | | | |
| 137 | 566.26 | 59.30 | | | |
| 138 | 463.79 | | 1704.9 ± 424.8 | | |
| 139 | 577.91 | | | | |
| 140 | 545.84 | | 1045.5 ± 256.3 | | |
| 141 | 487.81 | | | 365.5 ± 9.6 | |
| 142 | 464.78 | 76.10 | 1847.6 ± 1380.1 | | |
| 143 | 591.91 | 80.00 | 788.5 ± 202.3 | 952.8 ± 511.9 | |

TABLE 2-continued

| | | | | | |
|---|---|---|---|---|---|
| 144 | 619.97 | 89.50 | 140.1 ± 63.1 | 440.6 ± 72.3 | |
| 145 | 520.24 | 95.00 | 251.6 ± 75.1 | 157.0 ± 43.9 | |
| 146 | 536.24 | 94.80 | 81.9 ± 44.2 | 56.2 ± 8.1 | >10 μM |
| 147 | 492.18 | 99.50 | 251.1 ± 88.1 | 136.2 ± 17.6 | >10 μM |
| 148 | 485.79 | 94.50 | 591.6 ± 302.3 | 48.2 ± 3.5 | |
| 149 | 501.79 | 78.20 | 684.5 ± 428.1 | 331.8 ± 132.7 | |
| 150 | 506.21 | 91.40 | 703.7 ± 282.5 | 277.4 ± 34.0 | |
| 151 | 515.78 | 61.80 | 5969.0 ± 2597.0 | | |
| 152 | 540.66 | 90.50 | 711.0 ± 174.8 | 244.2 ± 49.5 | |
| 153 | 540.66 | 87.00 | 1056.2 ± 655.8 | 982.9 ± 140.2 | |
| 154 | 485.79 | 95.20 | 772.4 ± 446.3 | 204.2 ± 60.7 | |
| 155 | 485.79 | 85.00 | 473.3 ± 299.7 | 983.2 ± 19.4 | |
| 156 | 501.79 | 69.50 | | | |
| 157 | 507.75 | 95.20 | 217.1 ± 86.6 | 122.7 ± 42.8 | |
| 158 | 539.76 | 92.50 | 302.4 ± 132.5 | 237.0 ± 70.4 | |
| 159 | 506.2113 | 87.30 | 364.8 ± 160.2 | 132.8 ± 52.7 | |
| 160 | 489.76 | 88.20 | 262.2 ± 183.7 | 256.1 ± 98.7 | >10 μM |
| 161 | 489.76 | 87.70 | 529.5 ± 143.9 | 346.7 ± 45.6 | |
| 162 | 489.76 | 90.50 | 449.2 ± 67.9 | 235.2 ± 28.8 | >10 μM |
| 163 | 497.80 | 76.60 | 2072.5 ± 186.0 | 501.9 ± 182.6 | |
| 164 | 531.82 | 82.10 | 2831.0 ± 377.8 | 4031.8 ± 397.3 | |
| 165 | 507.75 | 89.80 | 151.5 ± 71.0 | 70.3 ± 0.5 | >10 μM |
| 166 | 507.75 | 88.30 | | 265.2 ± 53.6 | |
| 167 | 477.81 | 92.10 | | 431.9 ± 184.5 | |
| 168 | 471.77 | 93.90 | 203.5 ± 78.1 | 216.3 ± 60.7 | >10 μM |
| 169 | 503.78 | | | 357.0 ± 81.1 | |
| 170 | 524.20 | | 25.7 ± 2.9 | 35.1 ± 22.2 | >10 μM |
| 171 | 524.20 | | 11.6 ± 3.4 | 50.7 ± 11.8 | >10 μM |
| 172 | 844.40 | | | >10 μM | |
| 173 | 524.20 | | 19.3 ± 3.5 | 23.5 ± 11.2 | |
| 174 | 501.79 | | | 947.3 ± 207.4 | |
| 175 | 539.76 | | | 549.2 ± 90.8 | |
| 176 | 477.81 | | | 126.7 ± 49.6 | |
| 177 | 511.83 | | | 1190.3 ± 275.2 | |
| 178 | 554.90 | | | 1079.4 ± 157.2 | |
| 179 | 539.76 | | | 1013.6 ± 118.8 | |
| 180 | 479.79 | | | 6822.8 ± 1254.3 | |
| 181 | 574.21 | | | 55.3 ± 24.1 | |
| 182 | 574.21 | | | 37.0 ± 17.1 | |
| 183 | 574.21 | | | 67.5 ± 6.1 | |
| 184 | 542.19 | | 22.0 ± 6.1 | 22.0 ± 6.1 | >10 μM |
| 185 | 542.19 | | | 15.6 ± 3.4 | |
| 186 | 540.66 | | | 12.2 ± 5.4 | |

TABLE 2-continued

| | | | | |
|---|---|---|---|---|
| 187 | 540.66 | | 17.8 ± 6.7 | |
| 188 | 520.24 | 51.7 ± 15.5 | 27.6 ± 18.7 | >10 μM |
| 189 | 487.77 | | 3967.5 ± 1521.4 | |
| 190 | 542.19 | 45.9 ± 18.4 | 15.6 ± 3.4 | >10 μM |
| 191 | 540.66 | 48.9 ± 12.0 | 12.2 ± 5.4 | >10 μM |
| 192 | 540.66 | 64.8 ± 10.5 | 17.8 ± 6.7 | >10 μM |
| 193 | 520.24 | 51.7 ± 15.5 | 27.6 ± 18.7 | >10 μM |
| 194 | 536.01 | | 126.5 ± 18.5 | |
| 195 | 571.93 | | 119.6 ± 1.6 | |
| 196 | 534.02 | 124.7 ± 23.1 | | >10 μM |
| 197 | 564.03 | | 212.8 ± 79.0 | |
| 198 | 542.19 | 82.9 ± 7.0 | 80.3 ± 24.6 | >10 μM |
| 199 | 536.24 | | 258.5 ± 52.9 | |
| 200 | 575.10 | | 209.2 ± 78.7 | |
| 201 | 520.24 | | 141.6 ± 13.0 | |
| 202 | 520.24 | 48.0 ± 11.1 | 34.9 ± 13.9 | >10 μM |
| 203 | 512.26 | | 301.9 ± 66.8 | |
| 204 | 512.26 | | 111.3 ± 27.9 | |
| 205 | 520.24 | | 5.8 ± 1.5 | |
| 206 | 534.26 | | 99.9 ± 6.9 | |
| 207 | 485.79 | | 29.5 ± 5.6 | |
| 208 | 499.82 | 15.0 ± 1.8 | 18.2 ± 9.5 | 1.9 ± 0.1 μM |

[a] Displacement of specific [$^3$H]-CP55940 binding in HEK 293 cells stably transfected with human CB1 receptor.
[b] Percent inhibition at 10 μM.
[c] Fuctional activity (EC$_{50}$) determined by inhibition of Eu-GTP binding to hCB1 transfected HEK 293 membrane.

As shown in Tables 1 and 2, the compounds with an additional methylene group between the triazole and the carbonyl moiety have good antagonist efficacy to the CB1 receptor. Particularly, insertion of a methylene group can change the distance, disrupt the conjugation between the carbonyl group and the 1,2,3-triazole of ureas, and then make the orientation of the carbonyl group more flexible for interaction with Lys192-Asp366 residues of the CB1 receptor. Hence, the compounds inserted with a methylene group have good affinity to the CB1 receptor and can serve as CB1 antagonists.

In addition, the compounds, which are halogenated benzyl amides, exhibit excellent antagonist efficacy. These amide compounds were further tested in the affinity to the CB2 receptor, and the results showed that they have very low affinity to CB2 receptor. Such very low affinity means these amide compounds possess great selectivity between CB1 and CB2 receptors, and such a characteristic of CB1/CB2 selectivity is quite unusual among conventionally reported antagonists.

In conclusion, the 1,2,3-triazole derivatives of the present invention can be used as effective CB1 antagonists and have good selectivity of CB1 receptors over CB2 receptors.

Although the present invention has been explained in relation to its preferred embodiment, it is to be understood that many other possible modifications and variations can be made without departing from the scope of the invention as hereinafter claimed.

What is claimed is:

1. A compound of formula I

Ar—X—Y—Z            formula I and pharmaceutically acceptable salts, prodrugs and solvates thereof,
wherein Ar is

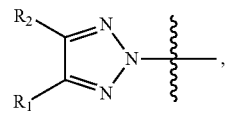

in which
R$_1$ and R$_2$ each independently represent phenyl, thienyl or pyridyl, each substituted by one or more halo;
X is —(CH$_2$)$_b$— in which b is 1, 2, 3 or 4;
Y is —C(O)— or —S(O$_2$)—; and
Z is NR$_4$R$_5$;
R$_4$ is H,

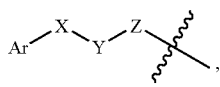

—(CH$_2$)$_r$(Ph)$_s$, —C$_{1-10}$ alkyl, C$_{2-10}$ alkenyl, C$_{2-10}$ alkynyl, C$_{5-9}$ aryl, C$_{4-9}$ cycloalkyl, carbamoyl, ureido, adamantyl, —CHR$_6$R$_7$, or C$_{4-9}$ heteroaryl or C$_{3-10}$ heterocycloalkyl comprising one to three heteroatoms which each independently are N, O, or S, in which R$_6$ and R$_7$ each independently are C$_{1-4}$ alkyl alcohol, C$_{1-4}$ alkyl or benzyl, with a proviso that one of R$_4$ and R$_5$ is not H and one of R$_6$ and R$_7$ is not H, wherein R$_6$ and R$_7$ are unsubstituted or optionally substituted by thiohydroxy, hydroxy, phenyl, nitro, or C$_{1-4}$ alkoxy;

R$_5$ is —(CH$_2$)$_r$(Ph)$_s$ or C$_{4-9}$ cycloalkyl;

wherein R$_4$, R$_5$, are unsubstituted or optionally further substituted by halo, hydroxy, cyano, nitro, thiohydroxy, amino, carbonyl, carbamoyl, sulfamoyl, C$_{1-4}$ alkyl, C$_{2-4}$ alkenyl, C$_{2-4}$ alkynyl, C$_{1-4}$ alkoxy, C$_{1-4}$ alkyl alcohol, C$_{1-4}$ haloalkyl, C$_{1-4}$ haloalkylthio, C$_{1-4}$ alkylamino, C$_{1-4}$ alkylamido, C$_{1-4}$ alkylsulfonyl, C$_{1-4}$ haloalkylsulfonyl, C$_{1-4}$ alkoxycarbonyl, C$_{1-4}$ alkylcarbamoyl, phenyl or benzyl;

r is 1, 2, 3, or 4; and s is 1 or 2.

2. The compound of claim 1, wherein R$_1$ and R$_2$ are phenyl.

3. The compound of claim 2, wherein the phenyl is substituted by one or more Cl.

4. The compound of claim 1, wherein Y is —C(O)—.

5. The compound of claim 1, wherein R$_4$ is H, C$_{4-8}$ alkyl, phenyl, benzyl, phenylethyl, phenylpropyl, cyclohexyl, propinylcyclohexyl, C$_{2-4}$ alkoxycarbonylmethyl, adamantyl, or six-membered heterocycloalkyl comprising one to two heteroatoms which each independently are N or O.

* * * * *